(12) United States Patent
Kurosawa et al.

(10) Patent No.: US 10,787,476 B2
(45) Date of Patent: Sep. 29, 2020

(54) GLYCOAMINO ACID AND USE THEREOF

(71) Applicant: AJINOMOTO CO., INC., Tokyo (JP)

(72) Inventors: Wataru Kurosawa, Kawasaki (JP); Risa Ubagai, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 291 days.

(21) Appl. No.: 15/078,305

(22) Filed: Mar. 23, 2016

(65) Prior Publication Data

US 2016/0200755 A1 Jul. 14, 2016

Related U.S. Application Data

(63) Continuation of application No. PCT/JP2014/075157, filed on Sep. 24, 2014.

(30) Foreign Application Priority Data

Sep. 24, 2013 (JP) ................. 2013-197165

(51) Int. Cl.
 *C07H 13/12* (2006.01)
(52) U.S. Cl.
 CPC ................. *C07H 13/12* (2013.01)
(58) Field of Classification Search
 CPC .......................................... C07H 13/12
 USPC ........................................ 514/25; 536/17.9
 See application file for complete search history.

(56) References Cited

U.S. PATENT DOCUMENTS

| | | | |
|---|---|---|---|
| 4,452,814 A | 6/1984 | Suami | |
| 5,212,298 A | 5/1993 | Rademacher et al. | |
| 5,280,113 A | 1/1994 | Rademacher et al. | |
| 5,935,635 A | 8/1999 | Mod et al. | |
| 6,576,620 B2 | 6/2003 | Belardinelli et al. | |
| 7,815,893 B2 | 10/2010 | Zander et al. | |
| 8,017,739 B2 | 9/2011 | Eichner et al. | |
| 8,475,765 B2 | 7/2013 | Zander et al. | |
| 8,618,266 B2 | 12/2013 | Conradt et al. | |
| 8,840,879 B2 | 9/2014 | Eichner et al. | |
| 2002/0155201 A1 | 10/2002 | Okada et al. | |
| 2005/0090053 A1 | 4/2005 | Temmler et al. | |
| 2005/0142278 A1 | 6/2005 | Okada et al. | |
| 2005/0234230 A1 | 10/2005 | Zander et al. | |
| 2005/0238723 A1 | 10/2005 | Zander et al. | |
| 2006/0019877 A1 | 1/2006 | Conradt et al. | |
| 2007/0134871 A1 | 6/2007 | Temmler et al. | |
| 2008/0206182 A1 | 8/2008 | Sommermeyer et al. | |
| 2008/0274948 A1 | 11/2008 | Eichner et al. | |
| 2009/0047251 A1 | 2/2009 | Eichner et al. | |
| 2010/0016547 A1 | 1/2010 | Ito et al. | |
| 2010/0050408 A1 | 3/2010 | Minor et al. | |
| 2010/0317609 A1 | 12/2010 | Zander et al. | |
| 2011/0054152 A1 | 3/2011 | Zander et al. | |
| 2011/0200555 A1 | 8/2011 | Eichner et al. | |
| 2011/0206794 A1 | 8/2011 | O'Kennedy | |
| 2012/0046240 A9 | 2/2012 | Zander et al. | |
| 2014/0147537 A1 | 5/2014 | O'Kennedy | |
| 2015/0044332 A1 | 2/2015 | Shi et al. | |
| 2015/0044347 A1 | 2/2015 | Shi et al. | |
| 2015/0064326 A1 | 3/2015 | Shi et al. | |
| 2015/0064327 A1 | 3/2015 | Shi et al. | |
| 2015/0072060 A1 | 3/2015 | Shi et al. | |
| 2015/0086694 A1 | 3/2015 | Shi et al. | |
| 2016/0256556 A1 | 9/2016 | Kasama et al. | |
| 2017/0181460 A1 | 6/2017 | Van Goudoever et al. | |
| 2017/0275666 A1 | 9/2017 | Prakash et al. | |
| 2017/0335302 A1 | 11/2017 | Peng et al. | |
| 2018/0169127 A1 | 6/2018 | Middleton et al. | |
| 2018/0256666 A1 | 9/2018 | O'Kennedy | |

FOREIGN PATENT DOCUMENTS

| | | | | |
|---|---|---|---|---|
| AU | A-48331/85 | * | 4/1985 | ............. C07H 13/12 |
| EP | 0 176 913 A2 | | 4/1986 | |
| EP | 0176913 A2 | * | 9/1986 | ............. C07H 13/12 |
| JP | 60-188037 A | | 9/1985 | |
| JP | 61-91194 | | 5/1986 | |
| JP | 61-91194 A | | 5/1986 | |
| JP | 61-124354 A | | 6/1986 | |
| JP | 3-83993 | | 4/1991 | |
| JP | 9-28310 | | 2/1997 | |
| JP | 10-165154 | | 6/1998 | |
| JP | 11-164675 | | 6/1999 | |

(Continued)

OTHER PUBLICATIONS

Moskovitz, H., Perception & Psychophysics, 1970, 7(5), 315-320.*
Tamura et al, Food Flavor and Safety-Molecular Analysis and Design, 1993, Chapter 12, pp. 158-169.*
Tamura et al, American Chemical Society, Food Flavor and Safety, 1993, vol. 526, Chapter 12, pp. 158-169.*
Kevin A. Francesconi, et al., "Arsenic Compounds from the Kidney of the Giant Clam Tridacna Maxima: Isolation and Identification of an Arsenic-Containing Nucleoside" Journal of the Chemical Society, Perkin Transactions 1, XP009159952, 1992, pp. 1349-1357.
International Search Report dated Nov. 25, 2014 in PCT/JP2014/075157 (with English language translation).
Kenneth J. Henry, Jr., et al., "Glycosylative transcarbamylation: efficient transformation of tert-butyl carbamates to novel glycoconjugates" Tetrahedron Letters, vol. 48, 2007, pp. 1791-1794.

(Continued)

*Primary Examiner* — Ganapathy Krishnan
(74) *Attorney, Agent, or Firm* — Oblon, McClelland, Maier & Neustadt, L.L.P.

(57) ABSTRACT

An object of the present invention is to provide glycoamino acid as an amino acid precursor with improved properties (particularly water-solubility, stability in water, bitter taste etc.). The present invention relates to a compound represented by the formula (I):

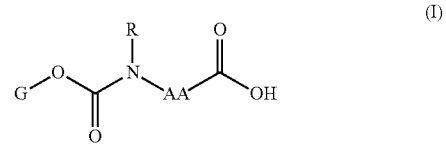

wherein each symbol is as defined in the DESCRIPTION, or a salt thereof.

13 Claims, 5 Drawing Sheets

(56) References Cited

FOREIGN PATENT DOCUMENTS

| | | |
|---|---|---|
| JP | 2002-262781 | 9/2002 |
| JP | 2004-59504 | 2/2004 |
| JP | 3527610 | 2/2004 |
| JP | 3585848 | 8/2004 |
| JP | 2006-70024 | 3/2006 |
| JP | 3855293 | 9/2006 |
| JP | 4335018 | 7/2009 |
| JP | 5454821 B2 | 1/2014 |
| JP | 2015-208241 | 11/2015 |
| JP | 2018-30888 | 3/2018 |
| JP | 6309343 | 3/2018 |
| JP | 6320367 | 4/2018 |
| JP | 6393468 | 8/2018 |
| WO | 01/40245 | 6/2001 |
| WO | 01/72138 A1 | 10/2001 |
| WO | 2004/067732 A2 | 8/2004 |
| WO | 2007-063907 A1 | 6/2007 |
| WO | 2011/119023 A1 | 9/2011 |
| WO | 2015/048339 A4 | 4/2015 |
| WO | 2015/048990 A1 | 4/2015 |
| WO | 2015/049294 A1 | 4/2015 |
| WO | 2015/050535 A1 | 4/2015 |
| WO | 2015/050537 A1 | 4/2015 |
| WO | 2016/126215 A1 | 8/2016 |
| WO | 2017/061582 A1 | 4/2017 |
| WO | 2018/109667 A1 | 6/2018 |

OTHER PUBLICATIONS

Masahiro Tamura, et al., "Molecular Design of Flavor Compounds Using O-Aminoacyl Sugars" American Chemical Society Symposium Series, Food Flavor and Safety, vol. 528, Chapter 12, 1993, pp. 158-169 (with Cover Page).
Thomas Kappes, et al., "The tetrabenzylglucosyloxycarbonyl(BGloc)-group-A carbohydrate-derived enzyme-labile urethane protecting group" Carbohydrate Research, vol. 305, 1998, pp. 341-349.
Andrew G. Gum, et al., "Enzyme-Labile Protecting Groups in Peptide Synthesis: Development of Glucose- and Galactose-Derived Urethanes" Chem. Eur. J., vol. 6, No. 20, 2000, pp. 3714-3721.
Paulsen et al., "Chemische Berichte", vol. 112, No. 12, pp. 3864-3878, (1979), considered only abstract in English for this document.
Garcia-Alles et al., "Tetrahedron", vol. 51, No. 1, pp. 307-316, (1995) and Chemical Abstract DN 122:240316 (RN 162103-99-3).
K. J. Henry, Jr. et al., "Tetrahedron Letters 48", (2007) pp. 1791-1794.
L. M. Likhosherstov et al., "Russ. Chem. Bull., Int. Ed.", vol. 67, No. 2, pp. 371-376, (2018).
L. M. Likhosherstov et al., "Russ. Chem. Bull., Int. Ed.", vol. 66, No. 4, pp. 717-720,(2017).
L. M. Likhosherstov et al., "Russ. Chem. Bull., Int. Ed.", (2016) vol. 65, No. 6, pp. 1617-1624.
N.A. Samoilova et al., "Journal of Applied Polymer Science", (2017), 134(16), 44718 (1 of 12) pages.
A. Kumar et al., "Journal of Biological Chemistry", (2016), 291(48), pp. 25032-25049.
V. Parmenopoulou et al., "Bioorganic & Medicinal Chemistry", (2014), 22(17), pp. 4810-4825.
V.M. Tran et al., "Bioconjugate Chem", (2014), vol. 25, pp. 262-268.
R. Uddin et al., "Med Chem Res", (2014) 23: pp. 2198-2206.
J. Verma, et al J. Chem. Inf. Model. (2009), 49, pp. 2695-2707.
L. M. Likhosherstov et al., "Russ. Chem. Bull., Int. Ed"., (2008), 57(11), pp. 2418-2422.
J.P.A. Martins et al., "Journal of Chemical Information and Modeling" (2009), 49(6), pp. 1428-1436.
D. Pan et al., "Journal of Medicinal Chemistry" (2004), 47(12), pp. 3075-3088.
K. Totani et al., "Bioorganic & Medicinal Chemistry Letters" (2004), 14(9), pp. 2285-2289.
D. Pan et al., "Journal of Chemical Information and Computer Sciences" (2003), 43(5), pp. 1591-1607.
I. Zamora et al., "Journal of Medicinal Chemistry" (2003), 46(1), pp. 25-33.
J. M. Risley et al., "Journal of Enzyme Inhibition" (2001), 16(3), pp. 269-274.
L. M. Kikhosherstov et al., "Russ. Chem. Bull. Int. Ed"., (2000), 49(8), pp. 1454-1459.
T. J. Tolbert et al., "Journal of the American Chemical Society" (2000), 122(23), pp. 5421-5428.
P. Venkatarangan et al., "Journal of Chemical Information and Computer Science" (1999), 39(6), pp. 1141-1150.
M. Pastor et al., "Journal of Medicinal Chemistry", (1997), 40(25), pp. 4089-4102.
M. Pastor et al., "Journal of Medicinal Chemistry", (1997), 40(10), pp. 1455-1464.
"Biochemistry", vol. 32, No. 14 (1993), 32(14), p. 3829.
I. D. Manger et al., "Biochemistry", (1992), 31(44), pp. 10724-10732.
M. E. Sant et al., "Journal of Biological Chemistry", (1992), 267(16), pp. 11038-11045.
M. Tamura et al., "Bulletin of the Chemical Society of Japan", (1984), 57(11), pp. 3167-3172.
M. Sawaki et al., "Chemical & Pharmaceutical Bulletin", (1984), 32(9), pp. 3698-3701.
"Journal of the American Chemical Society", (1983), 105(22), pp. 6745-6747.
B. Paul et al., "Carbohydrate Research", (1980), 80(1), pp. 99-115.
M.Y.H. Wong et al., "Carbohydrate Research", (1980), 80(1), pp. 87-98.
C. E. Benson et al., "Molecular and General Genetics", (1976), 145(1), pp. 31-36.
R. A. Woods et al., "Biochemical and Biophysical Research Communications", (1973), 53(3), pp. 787-793.
D. E. Cowley et al., "Carbohydrate Research", (1971), 19(2), pp. 231-241.
M. Kiyozumi et al., "Carbohydrate Research", (1970), 14(3), pp. 355-364 (see English Abstract).
R. J. Pollitt et al., "Clinica Chimica Acta", (1969), 25(3), pp. 413-416.
J. Yoshimura et al., "Carbohydrate Research", (1967), 5(1), pp. 82-92.
C. H. Bolton et al., "Biochemical Journal", (1966), 101(1), pp. 184-190.
A. Yamamoto et al., "Chemical & Pharmaceutical Bulletin", (1965), 13(9), pp. 1041-1046.
A. Yamamoto et al., "Chemical & Pharmaceutical Bulletin", (1965), vol. 13(9), 1036-1041.
R. D. Marshall et al., "Biochemistry", (1964), 3(10), pp. 1596-1600.
B. Anderson et al., "Biochimica et Biophysica Acta", (1963), 74(2), pp. 311-314.
S. G. Schultz et al., "Biochimica et Biophysica Acta" (1963), 71, pp. 505-508.
C. Coutsogeorgopoulos et al., "Journal of the American Chemical Society", (1961), 83, pp. 1885-1888.
J. Baddiley et al., "Journal of the Chemical Society", (1957) p. 4769.
J. Baddiley et al., "Journal of the Chemical Society", (1956) p. 2818.
S. C. Hartman et al., "Journal of Biological Chemistry", (1956), 221, pp. 1057-1070.
R. A. Peabody et al., "Journal of Biological Chemistry", (1956), 221, pp. 1071-1081.
Short Communications "Biochimica et Biophysica Acta", (1955), 18, pp. 148-149.
Short Communications "Biochimica et Biophysica Acta", (1955), 17, pp. 278-279.
Communications to the Editor "Journal of the American Chemical Society", (1954), 76, pp. 5258-5259.
A. N. Savel'ev et al., "Carbohydrate Research", (1996), 296, pp. 261-273.

(56) References Cited

OTHER PUBLICATIONS

X. Zhang et al., "Food Chemistry" (2018), 257, pp. 279-288.
G. Kronenberg et al., "Experimental Neurology"(2011), 228(2), pp. 253-258.
P. Gunasekara et al., Diabetes, Metabolic Syndrome and Obesity (2011), 4, pp. 53-60.
S. J. Duthie et al., "Cancer Prevention Research" (2010), 3(1), pp. 92-100.
CJ Prynne et al., "European Journal of Clinical Nutrition" (2009), 63(9), pp. 1084-1090.
G. Kronenberg et al., "Journal of Neuroscience" (2008), 28(28), pp. 7219-7230.
J. Holm et al., "Bioscience Reports" (2000), 20(2), pp. 109-118.

* cited by examiner

GLYCOAMINO ACID AND USE THEREOF

CROSS REFERENCES TO RELATED APPLICATIONS

This application is a continuation of International Patent Application No. PCT/JP2014/075157, filed on Sep. 24, 2014, and claims priority to Japanese Patent Application No. 2013-197165, filed on Sep. 24, 2013, all of which are incorporated herein by reference in their entireties.

BACKGROUND OF THE INVENTION

1. Field of the Invention

The present invention relates to a compound useful as an amino acid precursor and use thereof.

2. Discussion of the Background

While amino acid is utilized for a broad range of uses, the use thereof may be limited depending on the kind thereof due to the properties thereof. For example, since amino acids having low solubility in water (e.g., valine, leucine, isoleucine, tyrosine, cystine, phenylalanine, 3,4-dihydroxyphenylalanine etc.) cannot be easily dissolved in water at high concentrations, use thereof for aqueous compositions and liquid compositions is particularly subject to high restriction. When amino acids having low stability in water (e.g., cysteine, glutamine) are dissolved in water and used as liquid compositions and the like, the problems of decomposition, reaction of amino group with other components and the like, or the problems of coloration and odor tend to occur easily. In addition, amino acid with bitter tastes (e.g., valine, leucine, isoleucine) is under high restriction for oral use. As described above, since amino acid is restricted, due to its properties, particularly in the use as an aqueous composition and use for oral application, its use is sometimes difficult or formulation of a preparation requires some design.

On the other hand, a compound wherein amino group of amino acid is protected by a particular carbamate type sugar derivative is known (patent document 1, non-patent documents 1-3).

Non-patent document 1 discloses use of a glucose derivative wherein all hydroxyl groups are protected with a benzyl group as a carbamate type protecting group of an amino group in the peptide synthesis. After completion of the peptide synthesis, the sugar derivative is detached.

Non-patent document 2 discloses use of a glucose derivative wherein all hydroxyl groups are protected with an acetyl group as a carbamate type protecting group of an amino group in the peptide synthesis. After completion of the peptide synthesis, the sugar derivative is detached.

Non-patent document 3 discloses relating to the synthesis of a peptide fragment of natural product SQ-28546 that N-Boc-amino acid/peptide is converted to amino acid/peptide introduced with a glucosamine derivative, wherein all hydroxyl groups are protected with an acetyl group, as a carbamate type protecting group.

Patent document 1 discloses that, when a hydroxyl group of the side chain of a serine derivative wherein amino group is protected with an α,α-dimethyl-3,5-dimethoxybenzyloxycarbonyl group is reacted with glycosyl halide wherein all hydroxyl groups are protected with an acetyl group/benzyl group, α,α-dimethyl-3,5-dimethoxybenzyl group is transferred to form an ether bond with the side chain hydroxyl group, and a serine derivative wherein the above-mentioned glycosyl group is introduced as a carbamate type protecting group of the amino group is obtained, and discloses peptide synthesis utilizing such transfer reaction.

These documents do not disclose or suggest a glycoamino acid wherein hydroxyl groups of sugar derivatives are not protected or modified, and carboxy groups are not protected.

DOCUMENT LIST

Patent Documents patent document 1: JP-A-61-91194

Non-Patent Document non-patent document 1: Carbohydrate Research, 305, (1998) pp. 341-349 non-patent document 2: Chem. Eur. J., 2000, 6, No. 20, pp. 3714-3721 non-patent document 3: Tetrahedron Letters, 48, (2007) pp. 1791-1794

SUMMARY OF THE INVENTION

Problems to be Solved by the Invention

An object of the present invention is to provide a compound useful as an amino acid precursor with improved properties of amino acid (particularly water-solubility, stability in water, bitter taste etc.), and use thereof.

Means of Solving the Problems

In view of the above-mentioned problem, the present inventors have conducted intensive studies and found that introduction of a group represented by the formula G-O—C(O)— wherein G is a sugar residue wherein none of the hydroxyl groups are protected or modified into the amino group of amino acid improves the properties (particularly water-solubility, stability in water, bitter taste etc.) that the amino acid itself has, and the above-mentioned group represented by the formula G-O—C(O)— is detached from amino acid in vivo, which resulted in the completion of the present invention. The present invention is as described below.

[1] A compound represented by formula (I):

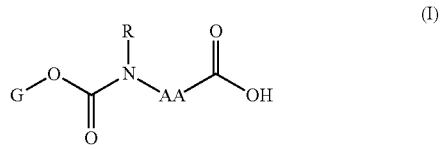

wherein
the moiety —NR-AA-C(=O)OH is an amino acid residue;
G is a sugar residue wherein none of the hydroxyl groups are protected or modified; and
R is a hydrogen atom or an alkyl group,
or a salt of said compound represented by formula (I),
with the proviso that said compound represented by formula (I) is not:
(1) a compound wherein G is a group represented by formula (II):

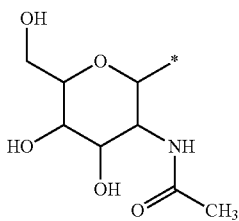 [SMILES: *C1OC(CO)C(O)C(O)C1NC(C)=O]

(II)

and the moiety —NR-AA-C(=O)OH is a lysine residue or a glutamic acid residue, or (2) a compound wherein G is a group represented by formula (III):

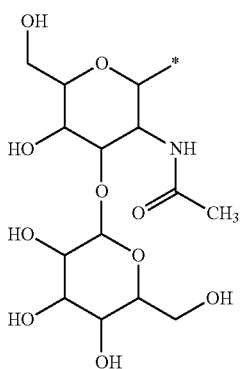 [SMILES: *C1OC(CO)C(O)C(OC2OC(CO)C(O)C(O)C2O)C1NC(C)=O]

(III)

and the moiety —NR-AA-C(=O)OH is a serine residue (hereinafter to be also referred to as compound (I)).

[2] The compound or salt of the above-mentioned [1], wherein the sugar of said sugar residue wherein none of the hydroxyl groups are protected or modified for G is monosaccharide.

[3] The compound or salt of the above-mentioned [1], wherein the sugar of said sugar residue wherein none of the hydroxyl groups are protected or modified for G is glucose, glucosamine, or N-acetylglucosamine.

[4] The compound or salt of the above-mentioned [1], wherein the moiety represented by formula G-O— has a β-anomer structure.

[5] The compound or salt of the above-mentioned [1], wherein the amino acid of said amino acid residue is an α-amino acid.

[6] The compound or salt of the above-mentioned [1], wherein the amino acid of said amino acid residue is valine, leucine, or isoleucine.

[7] The compound or salt of the above-mentioned [1], wherein the amino acid of said amino acid residue is phenylalanine, tyrosine, or 3,4-dihydroxyphenylalanine.

[8] The compound or salt of the above-mentioned [1], wherein R is a hydrogen atom.

[9] An aqueous composition, comprising a compound represented by formula (I) or salt thereof of the above-mentioned [1].

[10] An oral preparation, comprising a compound represented by formula (I) or salt thereof of the above-mentioned [1].

[11] A method of reducing a bitter taste of an amino acid, comprising introducing a group represented by formula G-O—C(O)—, wherein G is a sugar residue wherein none of the hydroxyl groups are protected or modified, into an amino group of amino acid.

[12] The method of the above-mentioned [11], wherein the sugar of said sugar residue wherein none of the hydroxyl groups are protected or modified for G is monosaccharide.

[13] The method of the above-mentioned [11], wherein the sugar of the sugar residue wherein none of the hydroxyl groups are protected or modified for G is glucose, glucosamine, or N-acetylglucosamine.

[14] The method of the above-mentioned [11], wherein the moiety represented by formula G-O— has a β-anomer structure.

[15] The method of the above-mentioned [11], wherein the amino acid of said amino acid residue is an α-amino acid.

[16] The method of the above-mentioned [11], wherein the amino acid of said amino acid residue is valine, leucine, or isoleucine.

[17] The method of the above-mentioned [11], wherein said amino acid in which a group represented by formula G-O—C(O)— has been introduced is converted to an amino acid in vivo.

[18] A method for administering an amino acid to a subject in need thereof, comprising administering a compound represented by formula (I) or salt thereof according to the above-mentioned [1] to said subject.

Effect of the Invention

In the compound (glycoamino acid) or a salt thereof of the present invention, since a group represented by the formula G-O—C(O)— wherein G is as defined above is introduced into an amino group of the amino acid, the properties (particularly water-solubility, stability in water, bitter taste etc.) that the amino acid itself has are improved, and they are suitable as an aqueous composition or for oral use. In addition, since the above-mentioned group represented by the formula G-O—C(O)— is detached from the amino acid in vivo, the glycoamino acid or a salt thereof of the present invention is highly useful as an amino acid precursor. Using such precursor having improved water-solubility even in amino acid having comparatively high water-solubility, the broad utility of amino acid in the preparation of an aqueous composition or liquid composition for oral ingestion, and the like is markedly improved.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
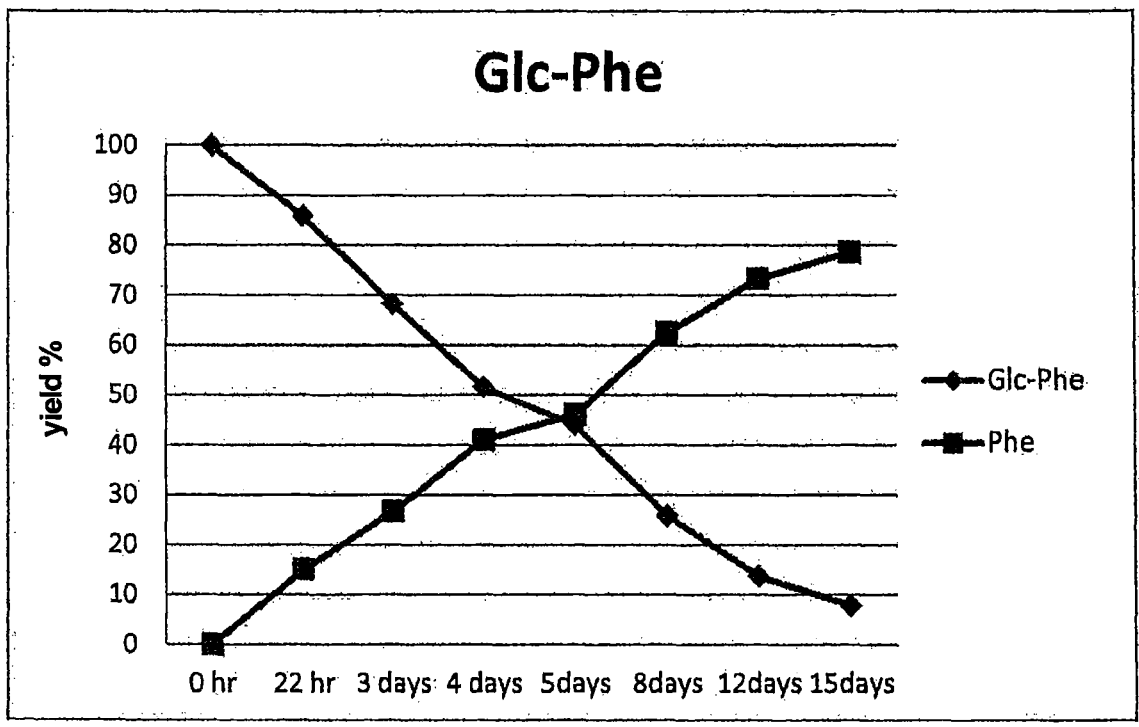
FIG. 1 shows an amino acid production amount from Glc-Phe in an artificial gastric juice.

Other features of the invention will become apparent in the course of the following descriptions of exemplary embodiments which are given for illustration of the invention and are not intended to be limiting thereof.

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the present specification are hereby incorporated by reference so as to describe and disclose constructed products and methodology described in, for example, publications usable in relation to the described invention.

The present invention is explained in detail in the following.

The moiety —NR-AA-C(=O)OH shows an amino acid residue.

The amino acid in the amino acid residue is not particularly limited as long as it has an amino group and a carboxy group, and may be any of α-amino acid, β-amino acid, γ-amino acid and the like. Examples of the α-amino acid include glycine, alanine, valine, leucine, isoleucine, serine, threonine, cysteine, methionine, glutamic acid, aspartic acid, lysine, arginine, histidine, glutamine, asparagine, phenylalanine, tyrosine, tryptophan, cystine, ornithine, thyroxin, proline, 3,4-dihydroxyphenylalanine and the like; examples of the β-amino acid include β-alanine and the like; and examples of the γ-amino acid include γ-aminobutyric acid and the like. When it has a functional group in the side chain, the functional group may be protected/modified as long as an adverse influence is not exerted on the properties (particularly water-solubility, stability in water, bitter taste etc.) of glycoamino acid.

Of these, α-amino acids such as valine, leucine, isoleucine, tyrosine, cystine, phenylalanine, 3,4-dihydroxyphenylalanine, cysteine, glutamine, glutamic acid, aspartic acid, lysine and the like are preferable, and introduction of a group represented by the formula G-O—C(O)— wherein G is as defined above into an amino group is effective for the improvement of the above-mentioned properties in amino acid showing low solubility in water (e.g., valine, leucine, isoleucine, tyrosine, cystine, phenylalanine, 3,4-dihydroxyphenylalanine etc.), amino acid showing low stability in water (e.g., cysteine, glutamine etc.), and amino acid having a bitter taste (e.g., valine, leucine, isoleucine etc.). Particularly, it is particularly effective for improving solubility in water and a bitter taste of valine, leucine and isoleucine.

The above-mentioned amino acid may be any of D form, L form and DL form.

G shows a sugar residue wherein none of the hydroxyl groups are protected or modified. That is, it is a sugar residue wherein all hydroxyl groups are free.

In the present specification, "a sugar residue wherein none of the hydroxyl groups are protected or modified" for G means a moiety of a sugar wherein all hydroxyl groups are free, which excludes a hemiacetal hydroxyl group. The sugar residue may be modified/altered as long as all hydroxyl groups are free. Examples of the "sugar residue wherein none of the hydroxyl groups are protected or modified" include monosaccharides such as glucose, glucosamine, N-acetylglucosamine, mannose, galactose, fructose, ribose, lyxose, xylose, arabinose and the like; a moiety of saccharides such as polysaccharide composed of these monosaccharides and the like, which excludes a hemiacetal hydroxyl group.

Of these, glucose residue, glucosamine residue and N-acetylglucosamine residue are preferable, glucose residue and N-acetylglucosamine residue are more preferable, and glucose residue is particularly preferable.

The above-mentioned saccharide may be any of D form and L form, and D form present in large amounts in nature is preferable.

A partial structure represented by the formula G-O— which is formed from the above-mentioned saccharides may be an α-anomer structure, a β-anomer structure or a mixture thereof, and a β-anomer structure is preferable.

R is a hydrogen atom or an alkyl group.

The "alkyl group" for R is a $C_{1-10}$ alkyl group, more preferably a $C_{1-6}$ alkyl group. Specific preferable examples include methyl, ethyl, propyl, isopropyl, butyl, isobutyl, sec-butyl, tert-butyl, pentyl, hexyl and the like.

R is preferably a hydrogen atom.

Compound (I) does not include (1) a compound wherein G is a group represented by the formula:

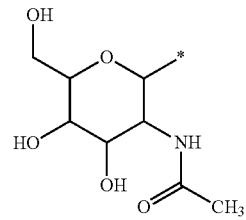

and AA is a lysine residue or a glutamic acid residue, and (2) a compound wherein G is a group represented by the formula:

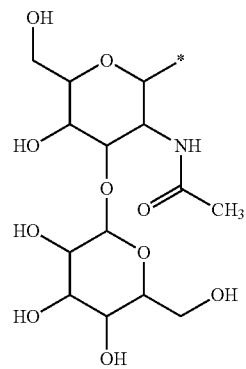

and AA is a serine residue.

Compound (I) is preferably a compound of the formula (I), wherein
AA is a valine residue, leucine residue or isoleucine residue;
G is a glucose residue, glucosamine residue or N-acetylglucosamine residue, wherein none of the hydroxyl groups are protected or modified; and
R is a hydrogen atom,
or a salt thereof.

Particularly preferably, it is a compound of the formula (I), wherein
AA is a valine residue, leucine residue or isoleucine residue;
G is a glucose residue wherein none of the hydroxyl groups are protected or modified; and
R is a hydrogen atom,
or a salt thereof.

In another embodiment,
compound (I) is preferably a compound of the formula (I), wherein
AA is a phenylalanine residue, tyrosine residue or 3,4-dihydroxyphenylalanine residue;
G is a glucose residue, glucosamine residue or N-acetylglucosamine residue, wherein none of the hydroxyl groups are protected or modified; and
R is a hydrogen atom,
or a salt thereof.

Particularly preferably, it is a compound of the formula (I), wherein
AA is a phenylalanine residue, tyrosine residue or 3,4-dihydroxyphenylalanine residue;
G is a glucose residue wherein none of the hydroxyl groups are protected or modified; and
R is a hydrogen atom,
or a salt thereof.

While the production method of the glycoamino acid and a salt thereof of the present invention is not particularly limited, for example, they can be synthesized by the following reactions.

Unless particularly indicated, the starting compound can be easily obtained as a commercially available product or can be produced by a method known per se or a method analogous thereto.

While the yield of the compound obtained by each of the following methods may vary depending on the reaction conditions to be used, the compound can be isolated and purified from the resultant products thereof by a conventional means (recrystallization, column chromatography etc.) and then precipitated by changing the solution temperature or solution composition and the like.

When an amino acid to be the starting compound in each reaction has a hydroxy group, an amino group, a carboxy group, a carbonyl group and the like on the side chain, a protecting group generally used in peptide chemistry and the like may be introduced into these groups, and the object compound can be obtained by removing the protecting group as necessary after the reaction.

Of compounds (I), compound (Ia) wherein R is a hydrogen atom can be produced, for example, by the following steps.

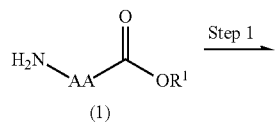

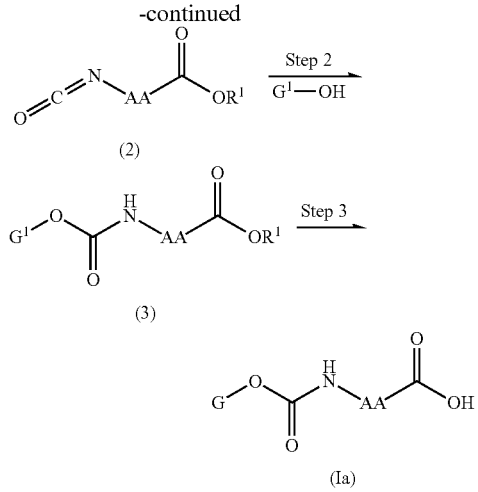

wherein $R^1$ is a carboxy-protecting group, $G^1$ is a sugar residue wherein all hydroxyl groups are protected, and other symbols are as defined above.

Examples of the carboxy-protecting group for $R^1$ include $C_{1-6}$ alkyl group (e.g., methyl, ethyl, tert-butyl), $C_{7-14}$ aralkyl group (e.g., benzyl etc.), trisubstituted silyl group (e.g., trimethylsilyl, triethylsilyl, dimethylphenylsilyl, tert-butyldimethylsilyl, tert-butyldiethylsilyl etc.) and the like. Of these, methyl, ethyl and benzyl are preferable.

Examples of the sugar residue wherein all hydroxyl groups are protected for $G^1$ include one wherein hydroxyl groups of "sugar residue wherein none of the hydroxyl groups are protected or modified" for G are substituted by a protecting group such as $C_{7-14}$ aralkyl group (e.g., benzyl etc.), $C_{1-6}$ alkyl-carbonyl group optionally substituted by a halogen atom (e.g., acetyl, chloroacetyl), benzoyl group, $C_{7-14}$ aralkyl-carbonyl group (e.g., benzylcarbonyl etc.), 2-tetrahydropyranyl group, 2-tetrahydrofuranyl group, trisubstituted silyl group (e.g., trimethylsilyl, triethylsilyl, dimethylphenylsilyl, tert-butyldimethylsilyl, tert-butyldiethylsilyl etc.) and the like. Of these, acetyl and benzyl are preferable. It is preferable that all hydroxyl groups be protected by the same protecting group.

step 1

In this step, an amino group of compound (1) or a salt thereof is converted to an isocyanato group to give compound (2).

This reaction is generally performed by reacting compound (1) or a salt thereof with di-tert-butyl dicarbonate ($Boc_2O$) in the presence of a base in a solvent that does not influence the reaction.

The amount of di-tert-butyl dicarbonate to be used is generally 0.7-5 mol, preferably 1-2 mol, per 1 mol of compound (1) or a salt thereof.

Examples of the base include 4-(dimethylamino)pyridine and the like.

The amount of the base to be used is generally 0.5-3 mol, preferably 1-2 mol, per 1 mol of compound (1) or a salt thereof.

While the solvent is not particularly limited as long as the reaction proceeds, for example, hydrocarbon (e.g., benzene, toluene, xylene, hexane, heptane etc.), halogenated hydrocarbon (e.g., chloroform, dichloromethane etc.), ether (e.g., diethyl ether, diisopropyl ether, tert-butyl methyl ether, tetrahydrofuran, 1,4-dioxane, 1,2-dimethoxyethane etc.) or a mixture thereof is used. Of these, dichloromethane is preferable.

The reaction temperature is generally −100 to 100° C., preferably −30 to 50° C., and the reaction time is generally 0.5-30 hr, preferably 1-5 hr.

After completion of the reaction, compound (2) is subjected to the next step in the form of a reaction mixture without isolation.

When compound (1) is in the form of an acid addition salt, it is treated with a base to be converted to a free form, and subjected to this step or reacted in the presence of excess base.

step 2

In this step, compound (2) is reacted with $G^1$-OH to give compound (3). $G^1$-OH is a sugar wherein all hydroxyl groups other than hemiacetal hydroxyl group are protected.

This reaction is generally performed by reacting compound (2) with $G^1$-OH in a solvent that does not influence the reaction.

The amount of $G^1$-OH to be used is generally 0.7-5 mol, preferably 1-2 mol, per 1 mol of compound (2).

While the solvent is not particularly limited as long as the reaction proceeds, for example, hydrocarbon (e.g., benzene, toluene, xylene, hexane, heptane etc.), halogenated hydrocarbon (e.g., chloroform, dichloromethane etc.), ether (e.g., diethyl ether, diisopropyl ether, tert-butyl methyl ether, tetrahydrofuran, 1,4-dioxane, 1,2-dimethoxyethane etc.) or a mixture thereof is used. Of these, dichloromethane is preferable.

The reaction temperature is generally −100-100° C., preferably −30-50° C. and the reaction time is generally 3-40 hr, preferably 10-30 hr.

The thus-obtained compound (3) can be isolated and purified by a known separation and purification means, for example, concentration, concentration under reduced pressure, solvent extraction, crystallization, recrystallization, phase transfer, chromatography and the like. Compound (3) may be m used for the next reaction without isolation.

step 3

In this step, the carboxy-protecting group of compound (3) and the hydroxyl-protecting group present in $G^1$ are removed to give compound (Ia) or a salt thereof.

Removal of the carboxy-protecting group and removal of the hydroxyl-protecting group present in $G^1$ may be performed simultaneously or in separate steps. In the latter case, the order thereof is not questioned but conveniently performed simultaneously. In this case, these protecting groups are selected to permit removal under the same conditions. For example, when the carboxy-protecting group for $R^1$ is methyl or ethyl, and the hydroxyl-protecting group present in $G^1$ is acetyl, they are removed by alkali hydrolysis.

Alkali hydrolysis is generally performed by treating compound (3) with alkali in a solvent that does not influence the reaction.

Examples of the alkali include lithium hydroxide, sodium hydroxide, potassium hydroxide, barium hydroxide and the like, and lithium hydroxide is preferable.

While the solvent is not particularly limited as long as the reaction proceeds, for example, water, alcohol (e.g., methanol, ethanol, isopropyl alcohol, tert-butyl alcohol etc.), ether (e.g., diethyl ether, diisopropyl ether, tert-butyl methyl ether, tetrahydrofuran, 1,4-dioxane, 1,2-dimethoxyethane etc.), halogenated hydrocarbon (e.g., dichloromethane etc.) or a mixture thereof is used. Of these, a mixture of water and alcohols (e.g., methanol, ethanol, isopropyl alcohol, tert-butyl alcohol etc.) is preferable.

The reaction temperature is generally −100-100° C., preferably −30-35° C. and the reaction time is generally 5-10 hr, preferably 0.5-2 hr.

The thus-obtained compound (Ia) or a salt thereof can be isolated and purified by a known separation and purification means, for example, concentration, concentration under reduced pressure, solvent extraction, crystallization, recrystallization, phase transfer, chromatography and the like.

Of compounds (I), a compound wherein R is an alkyl group can be obtained by introducing an alkyl group into compound (3) by a known method, and removing the protecting group in the same manner as in step 3. Examples of the method for introducing an alkyl group include a method including reacting compound (3) introduced with a base-resistant protecting group with the corresponding alkyl halide under appropriate basic conditions. Alternatively, an alkyl group is introduced in advance into amino group of compound (1) by a known method, and compound (I) can be obtained by a method similar to steps 1, 2 and 3.

The thus-obtained compound (I) can be isolated and purified by a known separation and purification means, for example, concentration, concentration under reduced pressure, solvent extraction, crystallization, recrystallization, phase transfer, chromatography and the like.

Compound (I) may be used in the form of a metal salt or a salt with an organic base, where necessary. When compound (I) is in the form of a salt, the salt thereof only needs to be a pharmacologically acceptable salt. For example, preferable examples of a salt with an acidic group such as carboxy group and the like include alkali metal salts such as sodium salt, potassium salt and the like; alkaline earth metal salts such as calcium salt, magnesium salt, barium salt and the like; ammonium salt, aluminum salt, zinc salt, salts with organic amine such as trimethylamine, triethylamine, pyridine, picoline, morpholine, pyrrolidine, piperidine, piperazine, 2,6-lutidine, ethanolamine, diethanolamine, triethanolamine, cyclohexylamine, dicyclohexylamine, N,N'-dibenzylethylenediamine and the like, and salts with basic amino acids such as arginine, lysine and the like. When compound (I) has a basic group such as amino group and the like, preferable examples of a salt with a basic group include salts with inorganic acids such as hydrochloric acid, sulfuric acid, phosphoric acid, nitric acid, hydrobromic acid and the like, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, salicylic acid, lactic acid, oxalic acid, mandelic acid, malic acid and the like, and salts with organic sulfonic acids such as methanesulfonic acid, benzenesulfonic acid, p-toluenesulfonic acid and the like.

In compound (I), since a group represented by the formula G-O—C(O)— wherein G is as defined above is introduced into an amino group of the amino acid, the properties (particularly water-solubility, stability in water, bitter taste etc.) that the amino acid itself has are improved. Therefore, improvement of water-solubility and stability in water expands application as an aqueous composition, and improvement of bitter taste renders the compound suitable for oral use.

In addition, since a group represented by the above-mentioned formula G-O—C(O)— is detached from amino acid under acidic conditions of gastric juice and the like or by glucosidase (particularly β-glucosidase), compound (I) is decomposed into amino acid in vivo. Therefore, compound (I) is useful as an amino acid precursor.

An aqueous N-(α/β-D-glucopyranosyloxycarbonyl)-L-leucine (Glc-Leu) solution (100 mg/dl) was heated for 72 hr (60° C., 90° C.), and free L-leucine (Leu) was analyzed over time by HPLC, whereby it was confirmed that about 50% of Leu was liberated at 90° C. in about 6 hr, and Leu was liberated almost completely in 72 hr. On the other hand, free Leu was not confirmed at 60° C. even after 72 hr, and sufficient heat stability as an amino acid precursor was shown.

EXAMPLES

The present invention is explained in more detail in the following by referring to Examples, which are not to be construed as limiting the scope of the present invention in any way. The reagents, apparatuses and materials used in the present invention are commercially available unless otherwise specified.

In the Examples,

Glc-XXX means amino acid (XXX) wherein amino group is carbamated with a D-glucopyranosyloxycarbonyl group, 4Ac-Glc-XXX means amino acid (XXX) wherein amino group is carbamated with a 2,3,4,6-tetra-O-acetyl-D-glucopyranosyloxycarbonyl group, GlcNAc-XXX means amino acid (XXX) wherein amino group is carbamated with a 2-acetamido-2-deoxy-D-glucopyranosyloxycarbonyl group, and 3Ac-GlcNAc-XXX means amino acid (XXX) wherein amino group is carbamated with a 2-acetamido-3,4,6-tri-O-acetyl-2-deoxy-D-glucopyranosyloxycarbonyl group.

In the present specification, when amino acid and the like are indicated by abbreviations, each indication is based on the abbreviation of the IUPAC-IUB Commission on Biochemical Nomenclature or conventional abbreviations in the art.

For example, amino acid (XXX) is indicated as follows.
Leu: L-leucine
Phe: L-phenylalanine
Lys: L-lysine
Glu: L-glutamic acid
Asp: L-aspartic acid
Val: L-valine
Ile: L-isoleucine
Tyr: L-tyrosine
DOPA: 3,4-dihydroxy-L-phenylalanine In the following Examples, "room temperature" shows generally about 10° C. to about 35° C. The ratio shown for mixed solvents is a volume mixing ratio unless otherwise specified.

$^1$H-NMR (proton nuclear magnetic resonance spectrum) was measured by Fourier-transform NMR. When protons of hydroxy group, carboxy group, amino group and the like have very mild peaks, they are not described.

Example 1 Glc-Leu; N-(α/β-D-glucopyranosyloxycarbonyl)-L-leucine

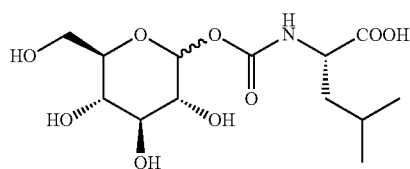 [SMILES: CC(C)C[C@H](NC(=O)OC1O[C@H](CO)[C@@H](O)[C@H](O)[C@H]1O)C(=O)O]

(1) 4Ac-Glc-Leu-OMe; N-(2,3,4,6-tetra-O-acetyl-α/β-D-glucopyranosyloxycarbonyl)-L-leucine methyl ester L-leucine methyl ester hydrochloride (293 mg, 1.61 mmol) was suspended in tetrahydrofuran (3.5 ml), and the suspension was cooled in an ice bath. To this suspension was added triethylamine (4.3 ml, 30.8 mmol), and the mixture was warmed to room temperature and stirred for 30 min. The reaction solution was filtered, and concentrated to give L-leucine methyl ester (232 mg, 1.61 mmol).

Boc$_2$O (493 mg, 2.26 mmol) was dissolved in dichloromethane (10 ml), and the mixture was cooled in an ice bath. To this solution were added a solution of 4-(dimethylamino)pyridine (198 mg, 1.62 mmol) in dichloromethane (7 ml) and a solution of L-leucine methyl ester (232 mg, 1.61 mmol) in dichloromethane (7 ml), and the mixture was stirred at room temperature for 1 hr. The reaction solution was cooled again in an ice bath, a solution of 2,3,4,6-tetra-O-acetyl-D-glucose (787 mg, 2.26 mmol) in dichloromethane (10 ml) was added, and the mixture was stirred for 18 hr. The reaction solution was concentrated under reduced pressure, and the residue was purified by silica gel column chromatography (gradient; hexane:ethyl acetate=85:15→60:40) to give 4Ac-Glc-Leu-OMe (698 mg, 1.34 mmol, yield 83%, α:β ratio=1:1) as a white powder.

$^1$H-NMR (400 MHz, CDCl$_3$) δ: 0.88-1.00 (m, 6H), 1.49-1.78 (m, 3H), 2.01 (s, 3H), 2.03 (s, 3H), 2.04 (s, 1.5H), 2.07 (s, 1.5H), 2.09 (s, 1.5H), 2.10 (s, 1.5H), 3.74 (s, 1.5H), 3.76 (s, 1.5H), 3.79-3.87 (m, 0.5H), 4.04-4.15 (m, 2H), 4.24-4.44 (m, 2H), 5.07-5.33 (m, 3.5H), 5.44-5.51 (m, 0.5H), 5.66 (d, 0.5H, J=8.2 Hz), 6.23 (d, 0.5H, J=3.5 Hz).

ESIMS (m/z): 542.2 ([M+Na]$^+$), 557.9 ([M+K]$^+$).

(2) Glc-Leu; N-(α/β-D-glucopyranosyloxycarbonyl)-L-leucine

4Ac-Glc-Leu-OMe (300 mg, 0.577 mmol) was dissolved in methanol (6 ml) and water (3 ml), and the mixture was cooled to −10° C. in a thermostatic bath. To this solution was added 1N aqueous lithium hydroxide solution (2.89 ml, 2.89 mmol), and the mixture was stirred for 10 min. To the reaction solution was added water (15 ml), and the mixture was stirred for 20 min. The reaction mixture was treated with a strong acid resin (Amberlite IR-120), and the resin was filtered off. The filtrate was concentrated under reduced pressure to give Glc-Leu (199 mg, yield quant., α:β ratio=1:1) as a white powder.

$^1$H-NMR (400 MHz, CD$_3$OD) δ: 0.93-1.02 (m, 6H), 1.58-1.85 (m, 3H), 3.34-3.59 (m, 3H), 3.65-3.90 (m, 3H), 4.17-4.25 (m, 1H), 5.35 (d, 0.5H, J=8.0 Hz), 5.96 (d, 0.5H, J=3.8 Hz).

ESIMS (m/z): 360.1 ([M+Na]$^+$), 376.1 ([M+K]$^+$).

Example 2 Glc-Phe; N-(α/β-D-glucopyranosyloxycarbonyl)-L-phenylalanine

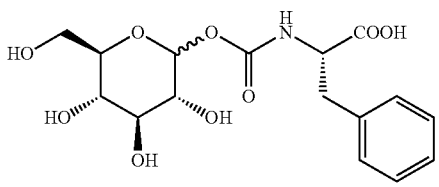 [SMILES: O=C(N[C@@H](Cc1ccccc1)C(=O)O)OC1O[C@H](CO)[C@@H](O)[C@H](O)[C@H]1O]

(1) 4Ac-Glc-Phe-OMe; N-(2,3,4,6-tetra-O-acetyl-α/β-D-glucopyranosyloxycarbonyl)-L-phenylalanine methyl ester L-phenylalanine methyl ester hydrochloride (319 mg, 1.48 mmol) was suspended in tetrahydrofuran (4 ml), and the suspension was cooled in an ice bath. To this suspension was added triethylamine (4 ml, 28.6 mmol), and the mixture was warmed to room temperature and stirred for 1 hr. The reaction solution was filtered, and concentrated to give L-phenylalanine methyl ester (254 mg, 1.42 mmol).

Boc$_2$O (431 mg, 1.98 mmol) was dissolved in dichloromethane (10 ml), and the mixture was cooled in an ice bath. To this solution was added a solution of 4-(dimethylamino)pyridine (172 mg, 1.40 mmol) in dichloromethane (7 ml) and a solution of L-phenylalanine methyl ester (254 mg, 1.42 mmol) in dichloromethane (8 ml), and the mixture was stirred at room temperature for 1 hr. The reaction solution was cooled again in an ice bath, a solution of 2,3,4,6-tetra-O-acetyl-D-glucose (682 mg, 1.96 mmol) in dichloromethane (10 ml) was added, and the mixture was stirred for 18 hr. The reaction solution was concentrated under reduced pressure, and the residue was purified by silica gel column chromatography (gradient; hexane:ethyl acetate=85:15→57:43) to give 4Ac-Glc-Phe-OMe (769 mg, 1.39 mmol, yield 94%, α:β ratio=1:1) as a white powder.

$^1$H-NMR (400 MHz, CDCl$_3$) δ: 2.01 (s, 3H), 2.03 (s, 3H), 2.04 (s, 3H), 2.09 (s, 3H), 3.05-3.21 (m, 2H), 3.72 (s, 1.5H), 3.75 (s, 1.5H), 3.79-3.86 (m, 0.5H), 4.05-4.14 (m, 1.5H), 4.22-4.34 (m, 2H), 4.56-4.69 (m, 1H), 5.04-5.50 (m, 4H), 5.65 (d, 0.5H, J=8.3 Hz), 6.24 (d, 0.5H, J=3.6 Hz), 7.08-7.15 (m, 2H), 7.22-7.36 (m, 5H).

ESIMS (m/z): 576.0 ([M+Na]$^+$), 592.1 ([M+K]$^+$).

(2) Glc-Phe; N-(α/β-D-glucopyranosyloxycarbonyl)-L-phenylalanine

4Ac-Glc-Phe-OMe (394 mg, 0.711 mmol) was dissolved in methanol (15 ml), and the mixture was cooled to −10° C. in a thermostatic bath. To this solution was added 1N aqueous lithium hydroxide solution (3.55 ml, 3.55 mmol), and the mixture was stirred for 15 min. To the reaction solution was added water (40 ml), and the mixture was stirred for 40 min. The reaction mixture was treated with strong acid resin (Amberlite IR-120), and the resin was filtered off. The filtrate was concentrated under reduced pressure to give Glc-Phe (262 mg, 0.705 mmol, yield 99%, α:β ratio=1:1) as a white powder.

$^1$H-NMR (400 MHz, CD$_3$OD) δ: 2.94-3.05 (m, 1H), 3.16-3.25 (m, 1H), 3.38-3.52 (m, 3H), 3.60-3.87 (m, 3H), 4.40-4.47 (m, 1H), 5.31 (d, 0.5H, J=8.1 Hz), 5.90 (d, 0.5H, J=3.8 Hz), 7.17-7.32 (m, 5H).

ESIMS (m/z): 370.1 ([M−H]$^-$), 741.1 ([2M−H]$^-$).

Example 3 Glu-Lys; N-α-(α/β-D-glucopyranosyloxycarbonyl)-L-lysine

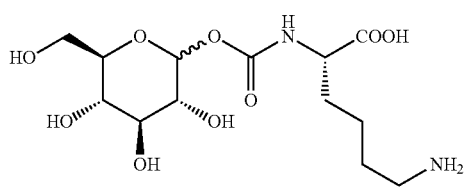 [SMILES: NCCCC[C@H](NC(=O)OC1O[C@H](CO)[C@@H](O)[C@H](O)[C@H]1O)C(=O)O]

(1) 4Ac-Glc-Lys(Z)-OMe; N-α-(2,3,4,6-tetra-O-acetyl-α/β-D-glucopyranosyloxycarbonyl)-N-ε-(benzyloxycarbonyl)-L-lysine methyl ester N-ε-(benzyloxycarbonyl)-L-lysine methyl ester hydrochloride (2.71 g, 8.21 mmol) was suspended in tetrahydrofuran (16 ml), and the suspension was cooled in an ice bath. To this suspension was added triethylamine (22.8 ml, 163 mmol), and the mixture was warmed to room temperature and stirred for 1 hr. The reaction solution was filtered, and concentrated to give N-ε-(benzyloxycarbonyl)-L-lysine methyl ester (2.48 g).

Boc$_2$O (2.48 g, 11.3 mmol) was dissolved in dichloromethane (30 ml), and the mixture was cooled in an ice bath. To this solution was added a solution of 4-(dimethylamino)pyridine (1.01 g, 8.28 mmol) in dichloromethane (30 ml) and a solution of N-ε-(benzyloxycarbonyl)-L-lysine methyl ester (2.48 g) in dichloromethane (30 ml), and the mixture was stirred at room temperature for 1 hr. The reaction solution was cooled again in an ice bath, a solution of 2,3,4,6-tetra-O-acetyl-D-glucose (4.00 g, 11.5 mmol) in dichloromethane (30 ml) was added, and the mixture was stirred for 18 hr. The reaction solution was concentrated under reduced pressure, and the residue was purified by silica gel column chromatography (gradient; hexane:ethyl acetate-70:30→40:60) to give 4Ac-Glc-Lys(Z)-OMe (3.75 g, 6.63 mmol, yield 81%, α:β ratio=1:1) as a white powder.

$^1$H-NMR (400 MHz, CDCl$_3$) δ: 1.31-1.94 (m, 6H), 2.00 (s, 1.5H), 2.01 (s, 1.5H), 2.02 (s, 1.5H), 2.03 (s, 1.5H), 2.05 (s, 1.5H), 2.05 (s, 1.5H), 2.07 (s, 1.5H), 2.09 (s, 1.5H), 3.12-3.24 (m, 2H), 3.74 (s, 1.5H), 3.76 (s, 1.5H), 3.72-3.83 (m, 0.5H), 4.07-4.18 (m, 1.5H), 4.24-4.40 (m, 2H), 4.79-4.89 (m, 1H), 5.04-5.27 (m, 2.5H), 5.43-5.57 (m, 1.5H), 5.64 (d, 0.5H, J=8.3 Hz), 6.22 (d, 0.5H, J=3.6 Hz), 7.27-7.40 (m, 5H).

ESIMS (m/z): 669.2 ([M+H]$^+$), 691.2 ([M+Na]$^+$), 707.2 ([M+K]$^+$), 667.2 ([M−H]$^-$), 971.4 ([2M−H]$^-$).

(2) Glc-Lys(Z); N-α-(α/β-D-glucopyranosyloxycarbonyl)-N-ε-(benzyloxycarbonyl)-L-lysine 4Ac-Glc-Lys(Z)-OMe (682 mg, 1.02 mmol) was dissolved in methanol (5.1 ml), and the mixture was cooled to −10° C. in a thermostatic bath. To this solution was added 1N aqueous lithium hydroxide solution (5.1 ml, 5.1 mmol), and the mixture was stirred for 15 min. To the reaction solution was added water (10 ml), and the mixture was stirred for 15 min. The reaction mixture was treated with strong acid resin (Amberlite IR-120), and the resin was filtered off. The filtrate was concentrated under reduced pressure to give Glc-Lys(Z) (510 mg, 1.04 mmol, yield quant., α:β ratio=1:1) as a white powder.

$^1$H-NMR (400 MHz, CD$_3$OD) δ: 1.38-1.95 (m, 6H), 3.09-3.20 (m, 2H), 3.35-3.46 (m, 2.5H), 3.50-3.57 (m, 0.5H), 3.61-3.88 (m, 3H), 4.03-4.22 (m, 1H), 5.08 (s, 2H), 5.36 (d, 0.5H, J=8.0 Hz), 5.97 (d, 0.5H, J=3.8 Hz), 7.26-7.43 (m, 5H).

ESIMS (m/z): 487.3 ([M+H]$^+$), 504.3 ([M+NH$_4$]$^+$), 509.1 ([M+Na]$^+$), 485.2 ([M−H]$^-$), 971.4 ([2M−H]$^-$).

(3) Glc-Lys; N-α-(α/β-D-glucopyranosyloxycarbonyl)-L-lysine

Glc-Lys(Z) (53.0 mg, 0.109 mmol) was dissolved in methanol (2 ml), 2% palladium carbon catalyst (26.3 mg, 50% (w/w)) was added, and the mixture was stirred under a hydrogen atmosphere (atmospheric) at room temperature for 3.5 hr. After completion of the reaction, the catalyst was filtered off. The filtrate was concentrated under reduced pressure to give Glu-Lys (35.0 mg, 0.993 mmol, yield 91%, α:β ratio=2:3) as a white powder.

$^1$H-NMR (400 MHz, D$_2$O) δ: 1.31-1.40 (m, 2H), 1.56-1.77 (m, 4H), 2.91 (t, 2H, J=7.5 Hz), 3.32-3.43 (m, 1H), 3.46-3.51 (m, 1H), 3.58-3.82 (m, 3H), 3.87-3.92 (m, 1H), 5.33 (d, 0.6H, J=8.1 Hz), 5.87 (d, 0.4H, J=3.7 Hz).

ESIMS (m/z): 353.2 ([M+H]⁺), 357.1 ([M+Na]⁺), 705.3 ([2M+H]⁺), 727.2 ([2M+Na]⁺), 351.1 ([M−H]⁻), 703.2 ([2M−H]⁻).

Example 4 Glc-Glu; N-(α/β-D-glucopyranosyloxy-carbonyl)-L-glutamic acid

[化 10]

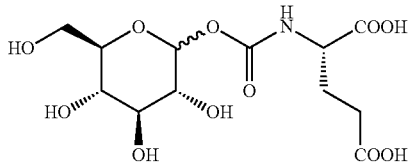 [SMILES: O=C(O)CC[C@H](NC(=O)OC1O[C@H](CO)[C@@H](O)[C@H](O)[C@H]1O)C(=O)O]

(1) 4Ac-Glc-Glu(OBn)-OMe; N-(2,3,4,6-tetra-O-acetyl-α/β-D-glucopyranosyloxycarbonyl)-L-glutamic acid γ-benzyl ester α-methyl ester In the same manner as in Example 1, step (1), 4Ac-Glc-Glu(OBn)-OMe (1.67 g) was obtained from L-glutamic acid γ-benzyl ester α-methyl ester hydrochloride (648 mg, 2.25 mmol) as a mixture with a sugar starting material.

ESIMS (m/z): 643.2 ([M+NH₄]⁺), 648.2 ([M+Na]⁺), 664.2 ([M+K]⁺).

(2) 4Ac-Glc-Glu-OMe; N-(2,3,4,6-tetra-O-acetyl-α/β-D-glucopyranosyloxycarbonyl)-L-glutamic acid α-methyl ester 4Ac-Glc-Glu(OBn)-OMe (582 mg; mixture with a sugar starting material) was dissolved in methanol (13 ml), 2% palladium carbon catalyst (582 mg, 100% (w/w)) was added, and the mixture was stirred under a hydrogen atmosphere (atmospheric) at room temperature for 3.5 hr. After completion of the reaction, the catalyst was filtered off. The filtrate was concentrated under reduced pressure, and the residue was purified by silica gel column chromatography (gradient; hexane:ethyl acetate=1:1→1:3) to give 4Ac-Glc-Glu-OMe (251 mg, 0.470 mmol, yield 60% (2 steps), α:β ratio=1:1) as a white powder.

¹H-NMR (400 MHz, CD₃OD) δ: 1.87-1.96 (m, 1H), 1.99-2.08 (m, 12H), 2.12-2.24 (m, 1H), 2.36-2.52 (m, 2H), 3.47 (s, 1.5H), 3.76 (s, 1.5H), 4.07-4.14 (m, 2H), 4.23-4.34 (m, 2H), 5.04-5.17 (m, 2H), 5.37 (t, 0.5H, J=9.5 Hz), 5.54 (t, 0.5H, J=9.7 Hz), 5.76 (d, 0.5H, J=8.3 Hz), 6.19 (d, 0.5H, J=3.2 Hz).

ESIMS (m/z): 536.2 ([M+H]⁺), 553.2 ([M+NH₄]⁺), 558.1 ([M+Na]⁺), 574.1 ([M+K]⁺), 533.9 ([M−H]⁻).

(3) Glc-Glu; N-(α/β-D-glucopyranosyloxycarbonyl)-L-glutamic acid

In the same manner as in Example 1, step (2), Glc-Glu (109 mg, 0.307 mmol, yield 79%, α:β ratio=2:3) was obtained as a white powder from 4Ac-Glc-Glu-OMe (208 mg, 0.388 mmol).

¹H-NMR (400 MHz, D₂O) δ: 1.83-1.93 (m, 1H), 2.05-2.15 (m, 1H), 2.40 (t, 2H, J=7.3 Hz), 2.47-2.60 (m, 2H), 3.55-3.78 (m, 4H), 4.11-4.17 (m, 1H), 5.29 (d, 0.6H, J=8.1 Hz), 5.84 (d, 0.4H, J=3.6 Hz).

ESIMS (m/z): 352.1 ([M−H]⁻).

Example 5 Glc-Asp; N-(α/β-D-glucopyranosyloxy-carbonyl)-L-aspartic acid

[化 11]

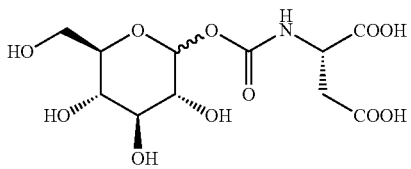 [SMILES: O=C(O)C[C@H](NC(=O)OC1O[C@H](CO)[C@@H](O)[C@H](O)[C@H]1O)C(=O)O]

(1) 4Ac-Glc-Asp(OBn)-OBn; N-(2,3,4,6-tetra-O-acetyl-α/β-D-glucopyranosyloxycarbonyl)-L-aspartic acid α-benzyl ester β-benzyl ester In the same manner as in Example 1, step (1), 4Ac-Glc-Asp(OBn)-OBn (1.18 g, 1.71 mmol, yield 60%, α:β ratio=3:2) was obtained as a pale-yellow powder from L-aspartic acid α-benzyl ester β-benzyl ester hydrochloride (1.00 g, 2.86 mmol).

¹H-NMR (400 MHz, CDCl₃) δ: 1.97-2.08 (m, 12H), 2.84-2.92 (m, 1H), 3.08-3.16 (m, 1H), 4.01-4.13 (m, 2H), 4.23-4.33 (m, 1H), 4.64-4.96 (m, 1H), 5.05-5.17 (m, 6H), 5.25 (t, 0.4H, J=9.4 Hz), 5.46 (t, 0.6H, J=9.9 Hz), 5.67 (d, 0.4H, J=8.4 Hz), 5.92 (d, 1H, J=8.5 Hz), 6.23 (d, 0.6H, J=3.7 Hz), 7.26-7.39 (m, 10H).

ESIMS (m/z): 705.2 ([M+NH₄]⁺), 710.2 ([M+Na]⁺), 726.1 ([M+K]⁺), 686.2 ([M−H]⁻)

(2) 4Ac-Glc-Asp; N-(2,3,4,6-tetra-O-acetyl-α/β-D-glucopyranosyloxycarbonyl)-L-aspartic acid In the same manner as in Example 4, step (2), 4Ac-Glc-Asp (411 mg, 0.810 mmol, yield quant., α:β ratio=3:2) was obtained as a white powder from 4Ac-Glc-Asp(OBn)-OBn (546 mg, 0.794 mmol).

¹H-NMR (400 MHz, CDCl₃) δ: 2.01-2.14 (m, 12H), 2.90-2.99 (m, 1H), 3.09-3.17 (m, 1H), 4.11-4.17 (m, 2H), 4.22-4.34 (m, ¹H), 4.63-4.70 (m, 1H), 5.06-5.17 (m, 2H), 5.30 (t, 0.4H, J=9.5 Hz), 5.54 (t, 0.6H, J=9.9 Hz), 5.69 (d, 0.4H, J=8.3 Hz), 6.22 (d, 0.6H, J=3.5 Hz), 6.43 (d, 0.4H, J=8.4 Hz), 6.51 (d, 0.6H, J=8.5 Hz)

ESIMS (m/z): 525.0 ([M+NH₄]⁺), 529.9 ([M+Na]⁺), 505.9 ([M−H]⁻).

(3) Glc-Asp; N-(α/β-D-glucopyranosyloxycarbo-nyl)-L-aspartic acid

In the same manner as in Example 1, step (2), Glc-Asp (109 mg, 0.307 mmol, yield 79%, α:β ratio=3:2) was obtained as a white powder from 4Ac-Glc-Asp (208 mg, 0.388 mmol).

¹H-NMR (400 MHz, CD₃OD) δ: 2.87-2.89 (m, 2H), 3.33-3.51 (m, 2H), 3.58-3.82 (m, 4H), 4.48-4.51 (m, 1H), 5.34 (d, 0.4H, J=8.1 Hz), 5.89 (d, 0.6H, J=3.6 Hz).

ESIMS (m/z): 357.1 ([M+NH₄]⁺), 362.1 ([M+Na]⁺), 337.9 ([M−H]⁻), 677.1 ([2M−H]⁻).

Example 6 Glc-DOPA; N-(α/β-D-glucopyranosyloxycarbonyl)-3,4-dihydroxy-L-phenylalanine

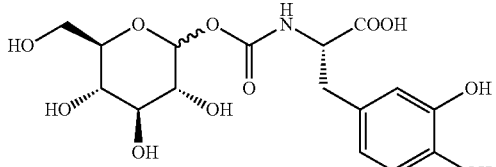

(1) DOPA-OMe hydrochloride; 3,4-dihydroxy-L-phenylalanine methyl ester hydrochloride Methanol (50 ml) was cooled to −5° C. in a thermostatic bath, and thionyl chloride (5 ml, 68.9 mmol) was added dropwise. Then, 3,4-dihydroxy-L-phenylalanine (10.0 g, 50.7 mmol) was added by small portions, and the mixture was stirred for 5 min. The mixture was warmed to room temperature, heated to 50° C., and stirred for 14 hr. The reaction solution was concentrated to give DOPA-OMe hydrochloride (14.3 g, 57.7 mmol, yield quant.) as an oil.

$^1$H-NMR (400 MHz, CD$_3$OD) δ: 3.04 (dd, 1H, J=7.4, 14.5 Hz), 3.13 (dd, 1H, J=5.8, 14.5 Hz), 3.84 (s, 3H), 4.22-4.25 (m, 1H), 6.58 (dd, 1H, J=2.2, 8.0 Hz), 6.69 (d, 1H, J=2.1 Hz), 6.77 (d, 1H, J=8.0 Hz).

ESIMS (m/z): 212.7 ([M+H]$^+$), 423.2 ([2M+H]$^+$), 210.2 ([M−H]$^-$), 241.1 ([M+Cl]$^-$).

(2) Boc-DOPA-OMe; N-(tert-butoxycarbonyl)-3,4-dihydroxy-L-phenylalanine methyl ester DOPA-OMe hydrochloride (1.26 g, 5.11 mmol) was dissolved in tetrahydrofuran (10 ml), saturated aqueous sodium bicarbonate solution (8 ml) was added, and the mixture was cooled in an ice bath. To this solution was added Boc$_2$O (1.00 ml, 4.35 mmol), and the mixture was warmed to room temperature and stirred for 1.5 hr. The reaction mixture was concentrated under reduced pressure, and dichloromethane (10 ml) and water (5 ml) were added to the residue, and the mixture was extracted twice with dichloromethane. The organic layer was washed with 10% aqueous citric acid solution (10 ml) and then with 15% brine (10 ml), and dried over magnesium sulfate. The desiccant was filtered off, and the filtrate was concentrated under reduced pressure. The obtained residue was purified by silica gel column chromatography (gradient; hexane:ethyl acetate=9:1→1:1) to give Boc-DOPA-OMe (980 mg, 3.15 mmol, yield 76%) as a pale-peach candy-like substance.

$^1$H-NMR (400 MHz, CDCl$_3$) δ: 1.42 (s, 9H), 2.89-3.01 (m, 2H), 3.71 (s, 3H), 4.49-4.54 (m, 1H), 5.01 (d, 1H, J=8.0 Hz), 5.51 (s, 1H), 5.65 (s, 1H), 6.54 (dd, 1H, J=1.5, 8.0 Hz), 6.65 (br, 1H), 6.76 (d, 1H, J=8.1 Hz).

ESIMS (m/z): 310.0 ([M−H]$^-$).

(3) Boc-DOPA(OBn)$_2$-OMe; N-(tert-butoxycarbonyl)-3,4-dibenzyloxy-L-phenylalanine methyl ester Boc-DOPA-OMe (984 mg, 3.15 mmol) was dissolved in N,N-dimethylformamide (20 ml), and the mixture was cooled in an ice bath. To this solution were added potassium carbonate (1.37 g, 9.92 mmol), and benzyl bromide (0.860 ml, 7.24 mmol), and the mixture was warmed to room temperature, heated to 50° C. and stirred for 1 hr. Diethyl ether (50 ml) and water (100 ml) were added, and the mixture was extracted twice with diethyl ether. The organic layer was washed with 15% brine (50 ml), and dried over magnesium sulfate. The desiccant was filtered off, and the filtrate was concentrated under reduced pressure to give Boc-DOPA(OBn)$_2$-OMe (1.37 g, 2.89 mmol, yield 88%) as a white powder.

$^1$H-NMR (400 MHz, CDCl$_3$) δ: 1.42 (s, 9H), 2.97-2.99 (m, 2H), 3.64 (s, 3H), 4.51-4.55 (m, 1H), 4.94 (d, 1H, J=7.2 Hz), 5.12 (s, 2H), 5.13 (s, 2H), 6.64 (dd, 1H, J=1.9, 8.2 Hz), 6.73 (d, 1H, J=2.0 Hz), 6.85 (d, 1H, J=8.2 Hz), 7.29-7.45 (m, 10H).

(4) DOPA(OBn)$_2$-OMe hydrochloride; 3,4-dibenzyloxy-L-phenylalanine methyl ester hydrochloride Boc-DOPA(OBn)$_2$-OMe (570 mg, 1.16 mmol) was dissolved in dichloromethane (6 ml), and the mixture was cooled in an ice bath. To this solution was added 4N hydrochloric acid/1,4-dioxane (2 ml), and the mixture was warmed to room temperature and stirred for 4 hr. The reaction solution was concentrated to give DOPA(OBn)$_2$-OMe hydrochloride (450 mg, 1.05 mmol, yield 91%) as a white powder.

$^1$H-NMR (400 MHz, CDCl$_3$) δ: 2.83 (dd, 1H, J=7.5, 13.7 Hz), 3.30 (dd, 1H, J=5.1, 13.6 Hz), 3.37 (s, 3H), 3.72-3.76 (m, 1H), 5.13 (s, 2H), 5.15 (s, 2H), 6.70 (dd, 1H, J=1.8, 8.2 Hz), 6.81 (d, 1H, J=1.9 Hz), 6.86 (d, 1H, J=8.2 Hz), 7.28-7.45 (m, 10H).

ESIMS (m/z): 302.2 ([M+H]$^+$), 414.3 ([M+Na]$^+$), 783.4 ([2M+H]$^+$), 806.4 ([2M+Na]$^+$).

(5) 4Ac-Glc-DOPA(OBn)$_2$-OMe; N-(2,3,4,6-tetra-O-acetyl-α/β-D-glucopyranosyloxycarbonyl)-3,4-dibenzyloxy-L-phenylalanine methyl ester In the same manner as in Example 1, step (1), 4Ac-Glc-DOPA(OBn)$_2$-OMe (808 mg) was obtained as a mixture with a sugar starting material from DOPA(OBn)$_2$-OMe hydrochloride (450 mg, 1.15 mmol).

(6) 4Ac-Glc-DOPA-OMe; N-(2,3,4,6-tetra-O-acetyl-α/β-D-glucopyranosyloxycarbonyl)-3,4-dihydroxy-L-phenylalanine methyl ester In the same manner as in Example 4, step (2), 4Ac-Glc-DOPA-OMe (298 mg, 0.509 mmol, yield 44% (2 steps), α:β ratio=1:1) was obtained as an oil from 4Ac-DOPA(OBn)$_2$-OMe (808 mg; mixture with a sugar starting material).

$^1$H-NMR (400 MHz, CDCl$_3$) δ: 2.02-2.18 (m, 12H), 2.97-3.07 (m, 2H), 3.76 (s, 1.5H), 3.78 (s, 1.5H), 4.10-4.19 (m, 1H), 4.21-4.47 (m, 1H), 4.53-4.68 (m, 1H), 5.05-5.17 (m, 1H), 5.21-5.28 (m, 1H), 5.50-5.64 (m, 2H), 5.67 (d, 0.5H, J=8.2 Hz), 6.34 (d, 0.5H, J=3.1 Hz), 6.41 (dd, 0.5H, J=2.0, 8.1 Hz), 6.48 (dd, 0.5H, J=1.9, 8.4 Hz), 6.50 (d, 0.5H, J=2.0 Hz), 6.65 (d, 0.5H, J=1.8 Hz), 6.77 (d, 0.5H, J=8.1 Hz), 6.82 (d, 0.5H, J=8.1 Hz).

ESIMS (m/z): 603.2 ([M+NH$_4$]$^+$), 608.2 ([M+Na]$^+$), 583.9 ([M−H]$^-$).

(7) Glc-DOPA; N-(α/β-D-glucopyranosyloxycarbonyl)-3,4-dihydroxy-L-phenylalanine In the same manner as in Example 1, step (2), Glc-DOPA (183 mg, 0.453 mmol, yield 89%, α:β ratio=1:1) was obtained as a pale-yellow powder from 4Ac-Glc-DOPA-OMe (298 mg, 0.509 mmol).

$^1$H-NMR (400 MHz, D$_2$O) δ: 2.77-2.84 (m, 1H), 2.97-3.03 (m, 1H), 3.30-3.45 (m, 2H), 3.53-3.78 (m, 4H), 4.28-4.37 (m, 1H), 5.25 (d, 0.5H, J=6.7 Hz), 5.77 (d, 0.5H, J=3.5 Hz), 6.59-6.63 (br, 1H), 6.69-6.70 (m, 1H), 6.73-6.77 (m, 1H).

ESIMS (m/z): 402.1 ([M−H]$^−$), 805.2 ([2M−H]$^−$).

Example 7 GlcNAc-Leu (α form, β form); N-(2-acetamido-2-deoxy-α-D-glucopyranosyloxycarbonyl)-L-leucine and N-(2-acetamido-2-deoxy-β-D-glucopyranosyloxycarbonyl)-L-leucine

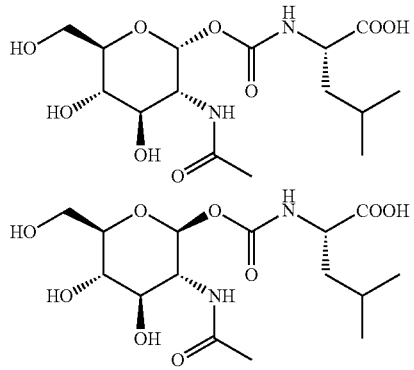

(1) 3Ac-GlcNAc-Leu-OMe (α form, β form); N-(2-acetamido-3,4,6-tri-O-acetyl-2-deoxy-α-D-glucopyranosyloxycarbonyl)-L-leucine methyl ester and N-(2-acetamido-3,4,6-tri-O-acetyl-2-deoxy-β-D-glucopyranosyloxycarbonyl)-L-leucine methyl ester In the same manner as in Example 1, step (1), L-leucine methyl ester hydrochloride (364 mg, 2.23 mmol) was desalted with triethylamine, a part (63.3 mg, 0.436 mmol) of the obtained L-leucine methyl ester (320 mg, 2.20 mmol) was reacted with 2-acetamido-3,4,6-tri-O-acetyl-2-deoxy-D-glucose to give α form (102 mg, 0.197 mmol, yield 45%) and β form (14.5 mg, 0.0280 mmol, yield 6%) of 3Ac-GlcNAc-Leu-OMe each as an oil.

$^1$H-NMR (400 MHz, CDCl$_3$) α form: δ: 0.97 (s, 3H), 0.98 (s, 3H), 1.52-1.62 (m, 1H), 1.65-1.74 (m, 1H), 1.94 (s, 3H), 2.04 (s, 3H), 2.05 (s, 3H), 2.09 (s, 3H), 3.76 (s, 3H), 4.05-4.09 (m, 1H), 4.26 (dd, 1H, J=3.9, 12.6 Hz), 4.37-4.43 (m, 1H), 4.46-4.52 (m, 1H), 5.15-5.27 (m, 2H), 5.63 (d, 1H, J=8.2 Hz), 5.84 (d, 1H, J=5.8 Hz), 6.06 (d, 1H, J=7.6 Hz).

ESIMS (m/z) α form: 519.2 ([M+H]$^+$), 536.2 ([M+NH$_4$]$^+$), 557.1 ([M+K]$^+$), 517.0 ([M−H]$^−$).

$^1$H-NMR (400 MHz, CDCl$_3$) β form: δ: 0.93 (s, 3H), 0.94 (s, 3H), 1.49-1.59 (m, 1H), 1.60-1.70 (m, 2H), 1.97 (s, 3H), 2.04 (s, 3H), 2.05 (s, 3H), 2.09 (s, 3H), 3.72 (s, 3H), 3.80-3.84 (m, 1H), 4.12 (dd, 1H, J=2.1, 12.4 Hz), 4.27-4.36 (m, 1H), 5.11-5.17 (m, 2H), 5.50 (d, 1H, J=8.5 Hz), 5.60 (d, 1H, J=8.9 Hz), 5.86 (d, 1H, J=9.6 Hz).

ESIMS (m/z) β form: 541.0 ([M+Na]$^+$), 557.1 ([M+K]$^+$), 517.2 ([M−H]$^−$).

(2-1) GlcNAc-Leu (α form); N-(2-acetamido-2-deoxy-α-D-glucopyranosyloxycarbonyl)-L-leucine In the same manner as in Example 1, step (2), GlcNAc-Leu (28.4 mg, 0.0751 mmol, yield 92%) was obtained as a white powder from 3Ac-GlcNAc-Leu-OMe (α form: 42.6 mg, 0.0822 mmol).

$^1$H-NMR (400 MHz, CD$_3$OD) δ: 0.94-0.99 (m, 6H), 1.63-1.66 (m, 2H), 1.71-1.81 (m, 1H), 1.98 (s, 3H), 3.31-3.34 (m, 1H), 3.46-3.53 (m, 1H), 3.71-3.81 (m, 2H), 3.99-4.02 (m, 1H), 4.19-4.22 (m, 1H), 6.01 (d, 1H, J=3.4 Hz).

ESIMS (m/z): 379.2 ([M+H]$^+$), 401.1 ([M+Na]$^+$), 779.3 ([2M+Na]$^+$), 377.2 ([M−H]$^−$), 755.3 ([2M−H]$^−$).

(2-2) GlcNAc-Leu (β form); N-(2-acetamido-2-deoxy-β-D-glucopyranosyloxycarbonyl)-L-leucine In the same manner as in Example 1, step (2), GlcNAc-Leu (9.5 mg, 0.025 mmol, yield 93%) was obtained as a white powder from 3Ac-GlcNAc-Leu-OMe (β form: 14.5 mg, 0.0280 mmol).

$^1$H-NMR (400 MHz, CD$_3$OD) δ: 0.94-0.97 (m, 6H), 1.53-1.66 (m, 2H), 1.67-1.77 (m, 1H), 1.99 (s, 3H), 3.37-3.40 (m, 2H), 3.47-3.52 (m, 1H), 3.72 (dd, 1H, J=5.0, 11.8 Hz), 3.84-3.91 (m, 2H), 4.11 (dd, 1H, J=5.1, 9.7 Hz), 5.43 (d, 1H, J=8.8 Hz).

ESIMS (m/z): 377.2 ([M−H]$^−$), 755.3 ([2M−H]$^−$).

Example 8 Glc-Val; N-(α/β-D-glucopyranosyloxycarbonyl)-L-valine

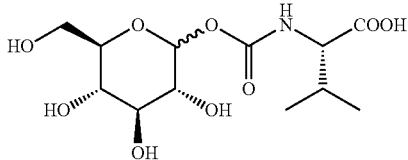

(1) 4Ac-Glc-Val-OMe; N-(2,3,4,6-tetra-O-acetyl-α/β-D-glucopyranosyloxycarbonyl)-L-valine methyl ester L-valine methyl ester hydrochloride (5.37 g, 32.1 mmol) was suspended in tetrahydrofuran (64 ml), and the suspension was cooled in an ice bath. To this suspension was added triethylamine (89 ml, 641 mmol), and the mixture was warmed to room temperature and stirred for 30 min. The reaction solution was filtered, and concentrated to give L-valine methyl ester (3.29 g, 25.1 mmol, yield 78%).

Boc$_2$O (7.70 ml, 35.1 mmol) was dissolved in dichloromethane (85 ml), and the mixture was cooled in an ice bath. To this solution was added a solution of 4-(dimethylamino)pyridine (3.37 g, 27.6 mmol) in dichloromethane (85 ml) and a solution of L-valine methyl ester (3.30 g, 25.1 mmol) in dichloromethane (85 ml), and the mixture was stirred at room temperature for 1 hr. The reaction solution was cooled again in an ice bath, a solution of 2,3,4,6-tetra-O-acetyl-D-glucose (11.9 g, 35.1 mmol) in dichloromethane (85 ml) was added and the mixture was stirred for 18 hr. The reaction solution was concentrated under reduced pressure, and the residue was purified by silica gel column chromatography (gradient; hexane:ethyl acetate=85:18→1:1) to give 4Ac-Glc-Val-OMe (3.95 g, 7.83 mmol, yield 31%, α:β ratio=3:2) as a pale-yellow powder.

$^1$H-NMR (400 MHz, CDCl$_3$) δ: 0.88-0.94 (m, 3H), 0.96-0.99 (m, 3H), 2.02-2.09 (m, 12H) 2.17-2.24 (m, 1H), 3.75 (s, 1.2H), 3.77 (s, 1.8H), 4.08-4.16 (m, 1H), 4.23-4.35 (m, 2H), 5.06-5.17 (m, 2H), 5.26 (t, 0.4H, J=9.4 Hz), 5.41 (t, 1H, J=9.7 Hz), 5.50 (t, 1H, J=9.9 Hz), 5.66 (d, 0.4H, J=8.2 Hz), 6.24 (d, 0.6H, J=3.7 Hz).

ESIMS (m/z): 523.2 ([M+NH$_4$]$^+$), 528.2 ([M+Na]$^+$), 522.0 ([M+Cl]$^-$).

(2) Glc-Val; N-(α/β-D-glucopyranosyloxycarbonyl)-L-valine

4Ac-Glc-Val-OMe (154 mg, 0.310 mmol) was dissolved in methanol (1.6 ml), and the mixture was cooled to −10° C. in a thermostatic bath. To this solution was added 1N aqueous lithium hydroxide solution (1.54 ml, 1.54 mmol), and the mixture was stirred for 10 min. To the reaction solution was added water (3.3 ml), and the mixture was stirred for 20 min. The reaction mixture was treated with strong acid resin (Amberlite IR-120), and the resin was filtered off. The filtrate was concentrated under reduced pressure to give Glc-Val (98.0 mg, 0.290 mmol, yield 98%, α:β ratio=3:7) as a pale-yellow powder.

$^1$H-NMR (400 MHz, CD$_3$OD) δ: 0.96-1.06 (m, 6H), 2.13-2.24 (m, 1H), 3.30-3.91 (m, 6H), 4.08-4.12 (m, 1H), 5.35 (d, 0.7H, J=7.9 Hz), 5.96 (d, 0.3H, J=3.8 Hz).

ESIMS (m/z): 322.2 ([M−H]$^-$), 645.2 ([2M−H]$^-$).

Example 9 Glc-Ile; N-(α/β-D-glucopyranosyloxycarbonyl)-L-isoleucine

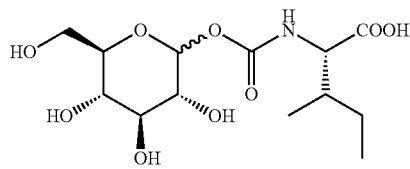 [SMILES: CCC(C)[C@H](NC(=O)OC1O[C@H](CO)[C@@H](O)[C@H](O)[C@H]1O)C(=O)O]

(1) 4Ac-Glc-Ile-OMe; N-(2,3,4,6-tetra-O-acetyl-α/β-D-glucopyranosyloxycarbonyl)-L-isoleucine methyl ester L-isoleucine methyl ester hydrochloride (3.00 g, 16.5 mmol) was suspended in tetrahydrofuran (33 ml), and the suspension was cooled in an ice bath. To this suspension was added triethylamine (46.0 ml, 330 mmol), and the mixture was warmed to room temperature and stirred for 1 hr. The reaction solution was filtered, and concentrated to give L-isoleucine methyl ester (2.13 g, 14.7 mmol).

Boc$_2$O (4.48 g, 20.5 mmol) was dissolved in dichloromethane (69 ml), and the mixture was cooled in an ice bath. To this solution was added a solution of 4-(dimethylamino)pyridine (1.97 g, 16.1 mmol) in dichloromethane (69 ml) and a solution of L-isoleucine methyl ester (2.13 g, 20.5 mmol) in dichloromethane (69 ml), and the mixture was stirred at room temperature for 1 hr. The reaction solution was cooled again in an ice bath, a solution of 2,3,4,6-tetra-O-acetyl-D-glucose (7.17 g, 20.5 mmol) in dichloromethane (69 ml) was added, and the mixture was stirred for 18 hr. The reaction solution was concentrated under reduced pressure, and the residue was purified by silica gel column chromatography (gradient; hexane:ethyl acetate=82:18→50:50) to give 4Ac-Glc-Ile-OMe (5.72 g, 11.0 mmol, yield 75%, α:β ratio=1:1) as a white syrup-like substance.

$^1$H-NMR (400 MHz, CDCl$_3$) δ: 0.89-0.95 (t, 6H, J=7.0 Hz), 1.13-1.27 (m, 1H), 1.37-1.46 (m, 1H), 1.86-1.94 (m, 1H), 2.01-2.09 (m, 12H), 3.73 (s, 1.5H), 3.76 (s, 1.5H), 3.80-3.84 (m, 0.5H), 4.07-4.14 (m, 1.5H), 4.25-4.36 (m, 2H), 5.08-5.17 (m, 2H), 5.25 (t, 0.5H, J=5.2 Hz), 5.41 (dd, 1H, J=5.4, 9.1 Hz), 5.47 (t, 0.5H, J=5.5 Hz), 5.65 (d, 0.5H, J=8.3 Hz), 6.24 (d, 0.5H, J=3.7 Hz).

ESIMS (m/z): 542.2 ([M+Na]$^+$), 558.1 ([M+K]$^+$).

(2) Glc-Ile; N-(α/β-D-glucopyranosyloxycarbonyl)-L-isoleucine

4Ac-Glc-Ile-OMe (1.01 g, 1.95 mmol) was dissolved in methanol (9.6 ml), and the mixture was cooled to −10° C. in an ice bath. To this solution was added 1N aqueous lithium hydroxide solution (9.75 ml, 9.75 mmol), and the mixture was stirred for 10 min. To the reaction solution was added water (19 ml), and the mixture was stirred for 15 min. The reaction mixture was treated with strong acid resin (Amberlite IR-120), and the resin was filtered off. The filtrate was concentrated under reduced pressure, and a similar operation was repeated 3 times in total (1N aqueous lithium hydroxide solution (6.9 ml, 14.1 ml, 20.0 ml)). The filtrate was concentrated under reduced pressure to give Glc-Ile (626 mg, 1.85 mmol, yield 95%, α:β ratio=1:1) as a white powder.

$^1$H-NMR (400 MHz, CD$_3$OD) δ: 0.91-0.98 (m, 6H), 1.21-1.29 (m, 1H), 1.44-1.56 (m, 1H), 1.82-1.94 (m, 1H), 3.35-3.42 (m, 1H), 3.53 (dd, 0.5H, J=3.8, 9.7 Hz), 3.66-3.85 (m, 4.5H), 4.10-4.17 (m, 1H), 5.33 (d, 0.5H, J=7.9 Hz), 5.94 (d, 0.5H, J=3.7 Hz).

ESIMS (m/z): 336.1 ([M−H]$^-$), 673.2 ([2M−H]$^-$).

Example 10 Glc-Tyr; N-(α/β-D-glucopyranosyloxycarbonyl)-L-tyrosine

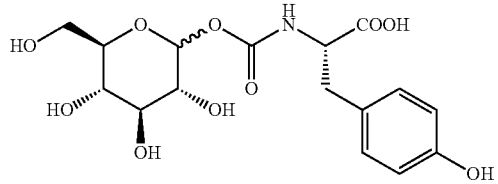 [SMILES: O=C(N[C@@H](Cc1ccc(O)cc1)C(=O)O)OC1O[C@H](CO)[C@@H](O)[C@H](O)[C@H]1O]

(1) 4Ac-Glc-Tyr(OBn)-OMe; N-(2,3,4,6-tetra-O-acetyl-α/β-D-glucopyranosyloxycarbonyl)-O-benzyl-L-tyrosine-O-benzyl methyl ester L-tyrosine methyl ester hydrochloride (2.00 g, 6.22 mmol) was suspended in tetrahydrofuran (30 ml), and the suspension was cooled in an ice bath. To this solution was added triethylamine (17.3 ml, 124 mmol), and the mixture was warmed to room temperature and stirred for 1 hr. The reaction solution was filtered and concentrated to give L-tyrosine methyl ester (1.81 g, 6.35 mmol).

Boc$_2$O (1.94 g, 8.89 mmol) was dissolved in dichloromethane (20 ml), and the mixture was cooled in an ice bath. To this solution was added a solution of 4-(dimethylamino)pyridine (853 mg, 6.99 mmol) in dichloromethane (20 ml) and a solution of L-tyrosine methyl ester (1.81 g, 6.35 mmol) in dichloromethane (20 ml), and the mixture was stirred at room temperature for 1 hr. The reaction solution was cooled again in an ice bath, a solution of 2,3,4,6-tetra-O-acetyl-D-glucose (3.10 g, 8.89 mmol) in dichloromethane (20 ml) was added, and the mixture was stirred for 16.5 hr. The reaction solution was concentrated under reduced pressure, and the residue was purified by silica gel column chromatography (gradient; hexane:ethyl acetate 70:30→40:60) to give 4Ac-Glc-Tyr(OBn)-OMe (3.10 g, 4.70 mmol, yield 76%, α:β ratio=3:2) as a pale-yellow syrup-like substance.

$^1$H-NMR (400 MHz, CDCl$_3$) δ: 2.00 (s, 1.5H), 2.01 (s, 1.5H), 2.03-2.04 (m, 6H), 2.08 (s, 1.5H), 2.09 (s, 1.5H), 3.01-3.13 (m, 2H), 3.72 (s, 1.5H), 3.74 (s, 1.5H), 4.09-4.15 (m, 2H), 4.24-4.34 (m, 1H), 4.53-4.64 (m, 1H), 5.02-5.50 (m, 6H), 5.65 (d, 0.4H, J=8.4 Hz), 6.24 (d, 0.6H, J=3.6 Hz), 6.87-6.96 (m, 2H), 7.00-7.05 (m, 2H), 7.31-7.44 (m, 5H).

ESIMS (m/z): 682.2 ([M+Na]$^+$), 698.2 ([M+K]$^+$).

(2) 4Ac-Glc-Tyr(OBn)-OMe; N-(2,3,4,6-tetra-O-acetyl-α/β-D-glucopyranosyloxycarbonyl)-L-tyrosine methyl ester 4Ac-Glc-Tyr(OBn)-OMe (3.09 g, 4.69 mmol) was dissolved in a mixed solution (60 ml) of methanol:ethyl acetate=1:1 and deaerated. 5% palladium/carbon (3.00 g, 100% (w/w)) was added, the inside of the container was replaced with hydrogen, and the mixture was stirred for 1 hr. Since the remainder of the starting material was confirmed, 5% palladium/carbon (1.50 g, 50% (w/w)) was added again, the inside of the container was replaced with hydrogen, and the mixture was further stirred for 2.5 hr. Palladium/carbon was filtered off, and the filtrate was concentrated under reduced pressure to give Glc-Tyr-OMe (2.78 g, 4.88 mmol, yield 92%, α:β ratio=1:1).

$^1$H-NMR (400 MHz, CDCl$_3$) δ: 2.00 (s, 1.5H), 2.01 (s, 1.5H), 2.03 (s, 3H), 2.05 (s, 1.5H), 2.06 (s, 1.5H), 2.09 (s, 1.5H), 2.10 (s, 1.5H), 2.91-3.13 (m, 2H), 3.70-3.81 (m, 0.5H), 3.76 (s, 1.5H), 3.76 (s, 1.5H), 4.06-4.28 (m, 2.5H), 4.53-4.63 (m, 1H), 5.06-5.49 (m, 4H), 5.59 (d, 0.5H, J=8.4 Hz), 6.23 (d, 0.5H, J=3.6 Hz), 6.71-6.80 (m, 2H), 6.96-7.00 (m, 2H).

ESIMS (m/z): 592.2 ([M+Na]$^+$).

(3) Glc-Tyr; N-(α/β-D-glucopyranosyloxycarbonyl)-L-tyrosine

4Ac-Glc-Tyr-OMe (1.00 g, 1.76 mmol) was dissolved in methanol (8.8 ml), and the mixture was cooled to −5° C. in a thermostatic bath. To this solution was added 1N aqueous lithium hydroxide solution (17.6 ml, 17.6 mmol), and the mixture was stirred for 25 min. The reaction mixture was treated with strong acid resin (Amberlite IR-120), and the resin was filtered off. The filtrate was concentrated under reduced pressure to give Glc-Tyr (702 mg, 1.81 mmol, yield quant., α:β ratio=3:2) as a white powder.

$^1$H-NMR (400 MHz, CD$_3$OD) δ: 2.87-2.95 (m, 1H), 3.10 (dd, 1H, J=5.1, 14.0 Hz), 3.50-3.54 (dd, 3H, J=3.8, 9.9 Hz), 3.64-3.85 (m, 3H), 4.34-4.39 (m, 1H), 5.31 (d, 0.4H, J=8.1 Hz), 5.91 (d, 0.6H, J=3.8 Hz), 6.71 (d, 0.6H, J=8.5 Hz), 6.72 (d, 0.4H, J=8.6 Hz), 7.07 (d, 0.4H, J=8.6 Hz), 7.08 (d, 0.6H, J=8.5 Hz).

ESIMS (m/z): 386.1 ([M−H]$^−$), 773.2 ([2M−H]$^−$).

Experimental Example 1

Figure 2:
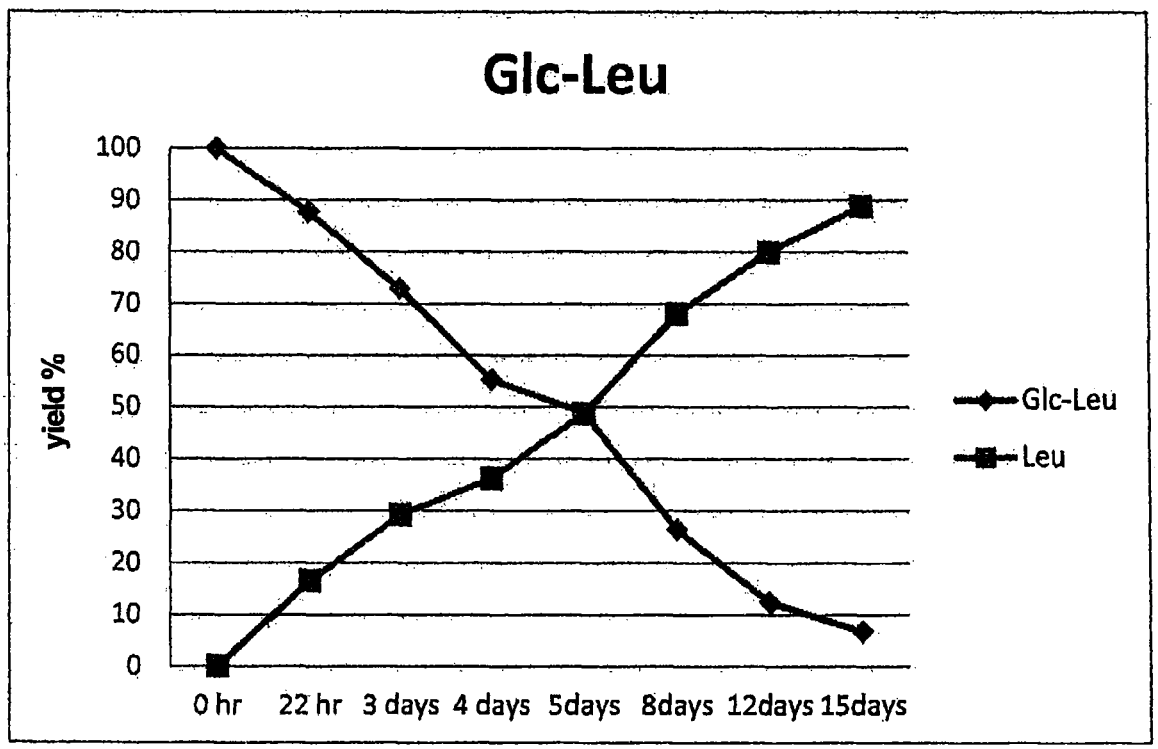
FIG. 2 shows an amino acid production amount from Glc-Leu in an artificial gastric juice.
Figure 3:
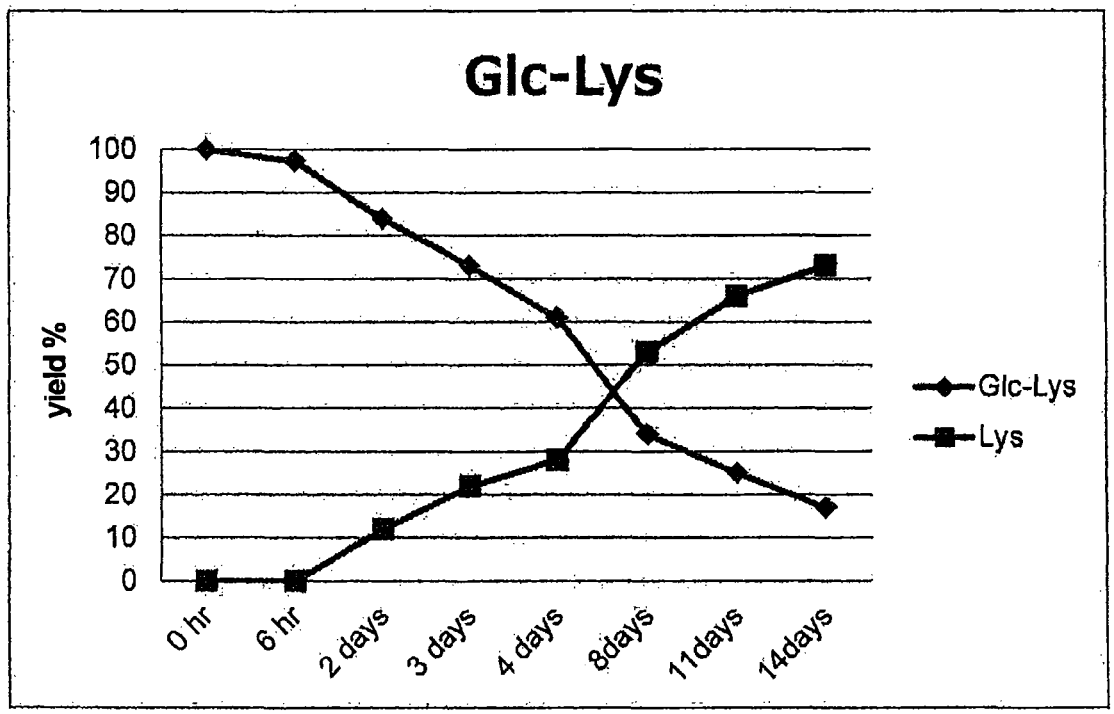
FIG. 3 shows an amino acid production amount from Glc-Lys in an artificial gastric juice.
Figure 4:
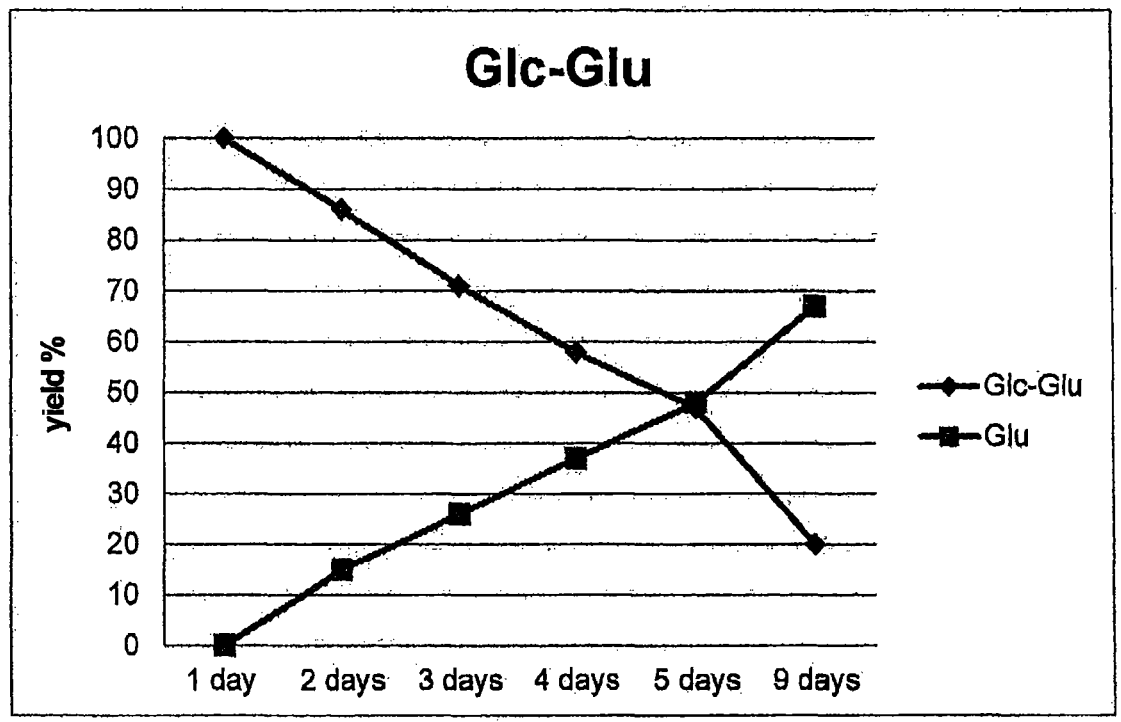
FIG. 4 shows an amino acid production amount from Glc-Glu in an artificial gastric juice.

Glc-Phe, Glc-Leu, Glc-Lys and Glc-Glu were each treated with artificial gastric juice (the Japanese Pharmacopoeia, 15th edition), and the amount of the resulting amino acid was measured. Each compound was dissolved in artificial gastric juice at the ratio shown in Table 1, and the mixture was stirred in a hot-water bath at 37° C., and analyzed by HPLC. The results thereof are shown in FIGS. 1-4. In the case of Glc-Phe and Glc-Leu, about 40% of amino acid in each starting material was liberated on day 4 and about 80-90% of amino acid was liberated on day 15. In the case of Glc-Lys, about 30% of lysine was liberated on day 4 and about 50% of lysine was liberated on day 8. In the case of Glc-Glu, about 40% of glutamic acid was liberated on day 4, and about 70% of glutamic acid was liberated on day 9.

HPLC analysis conditions were as described below.
column: CAPCELLPAK MG (4.6×250 mm, 5 μm)
column temperature: 40° C.
mobile phase: A: 100 mM KH$_2$PO$_4$, 5 mM sodium 1-octanesulfonate (pH 2.2)
B: acetonitrile
eluent: Glc-Leu, Glc-Phe: A/B=90/10, Glc-Lys: A/B=97/3, Glc-Glu: A/B=99/1
flow rate: Glc-Leu, Glc-Phe: 1.5 ml/min, Glc-Lys, Glc-Glu: 1.0 ml/min
detection: photodiode array detector measurement wavelength 210 nm
injection volume: 10 μL

TABLE 1

| | glycoamino acid (mg) | artificial gastric juice (ml) |
|---|---|---|
| Glc-Phe | 5.4 | 10 |
| Glc-Leu | 5.5 | 5 |
| Glc-Lys | 4.2 | 2 |
| Glc-Glu | 2.3 | 1 |

Experimental Example 2

Figure 5:
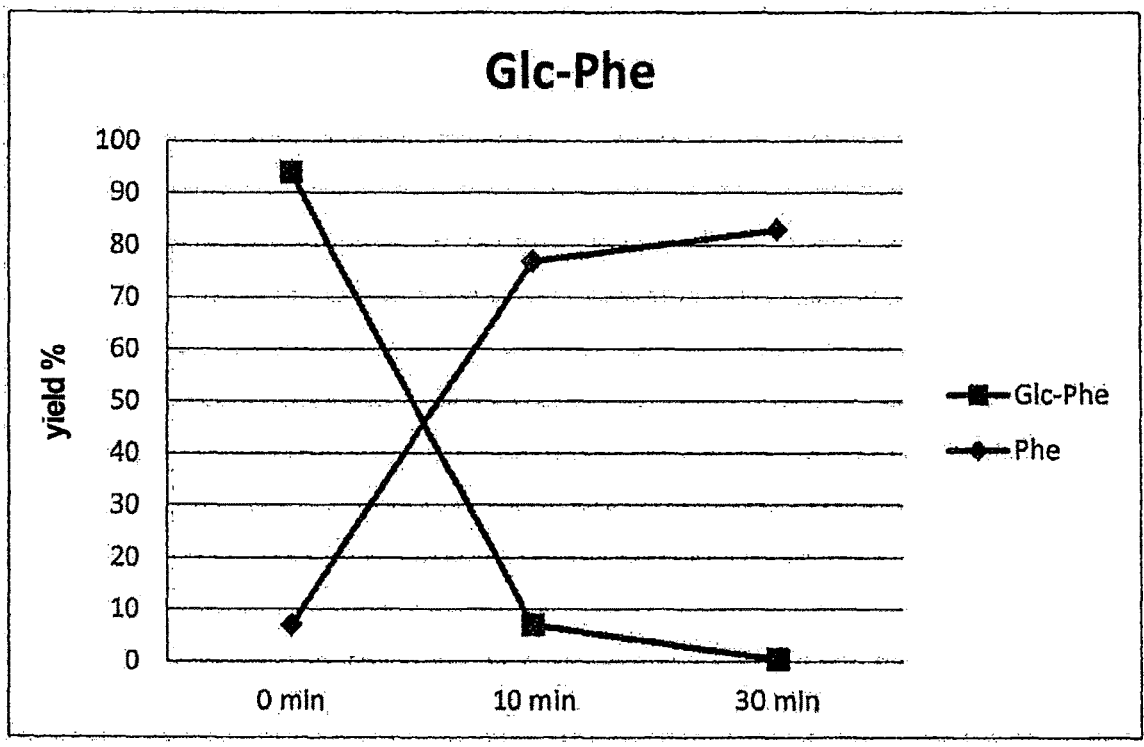
FIG. 5 shows an amino acid production amount by a glucosidase treatment of Glc-Phe.
Figure 6:
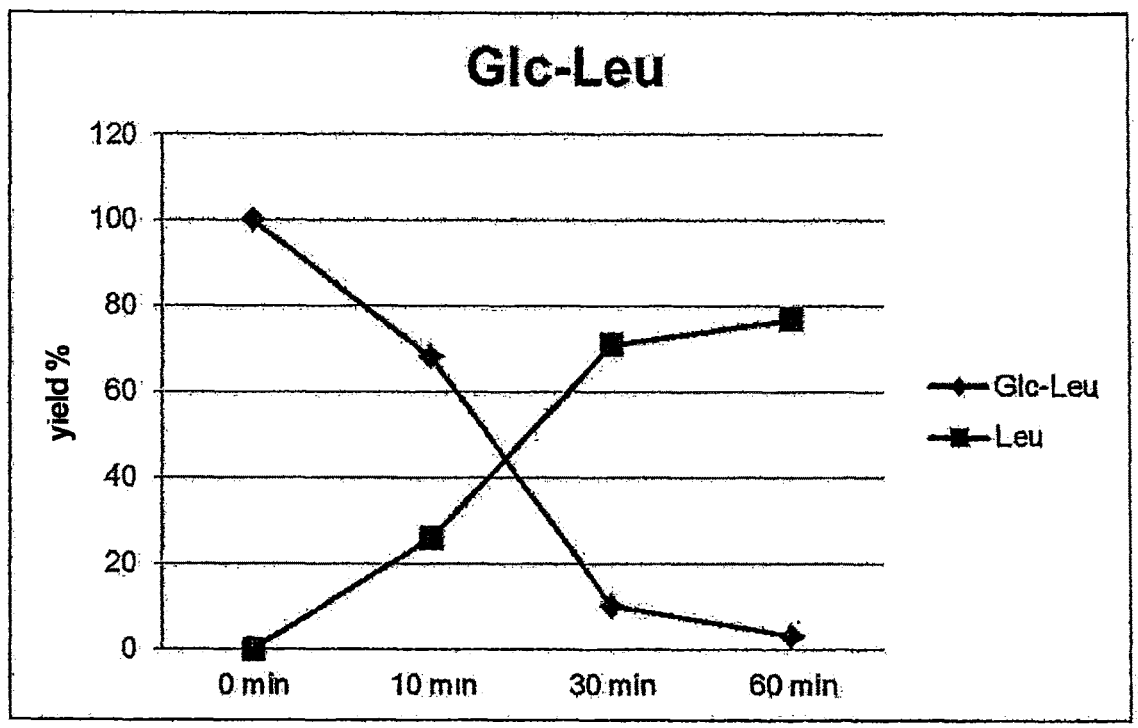
FIG. 6 shows an amino acid production amount by a glucosidase treatment of Glc-Leu.
Figure 7:
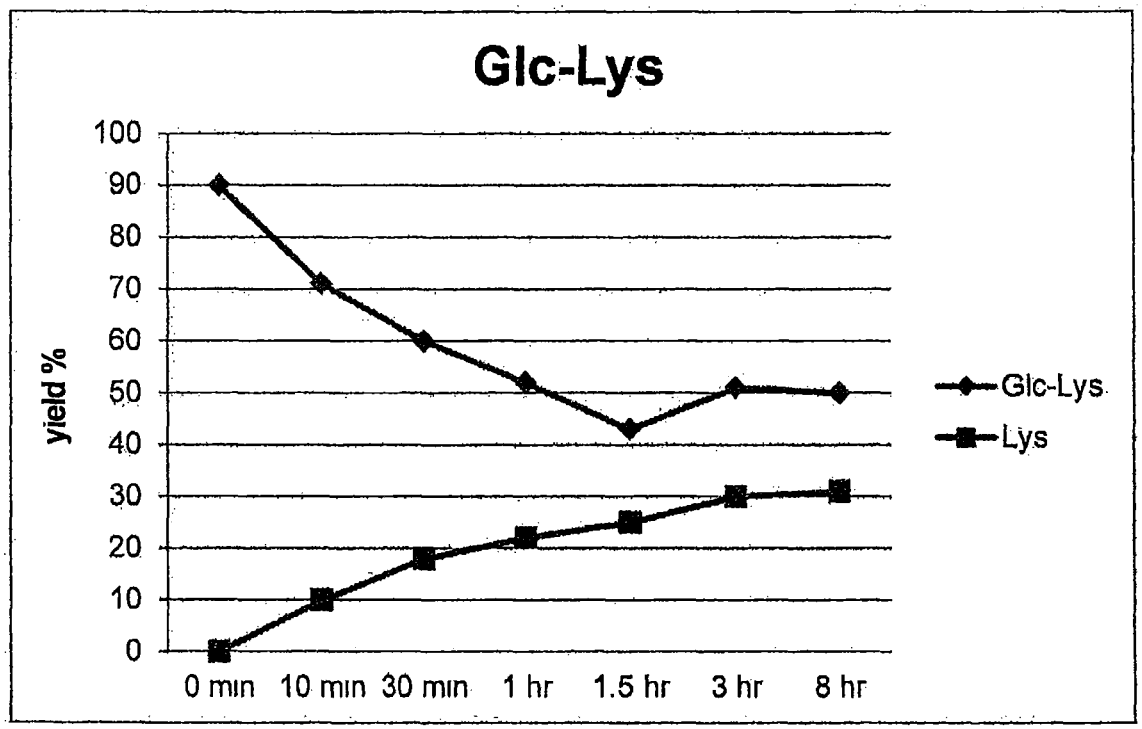
FIG. 7 shows an amino acid production amount by a glucosidase treatment of Glc-Lys.
Figure 8:
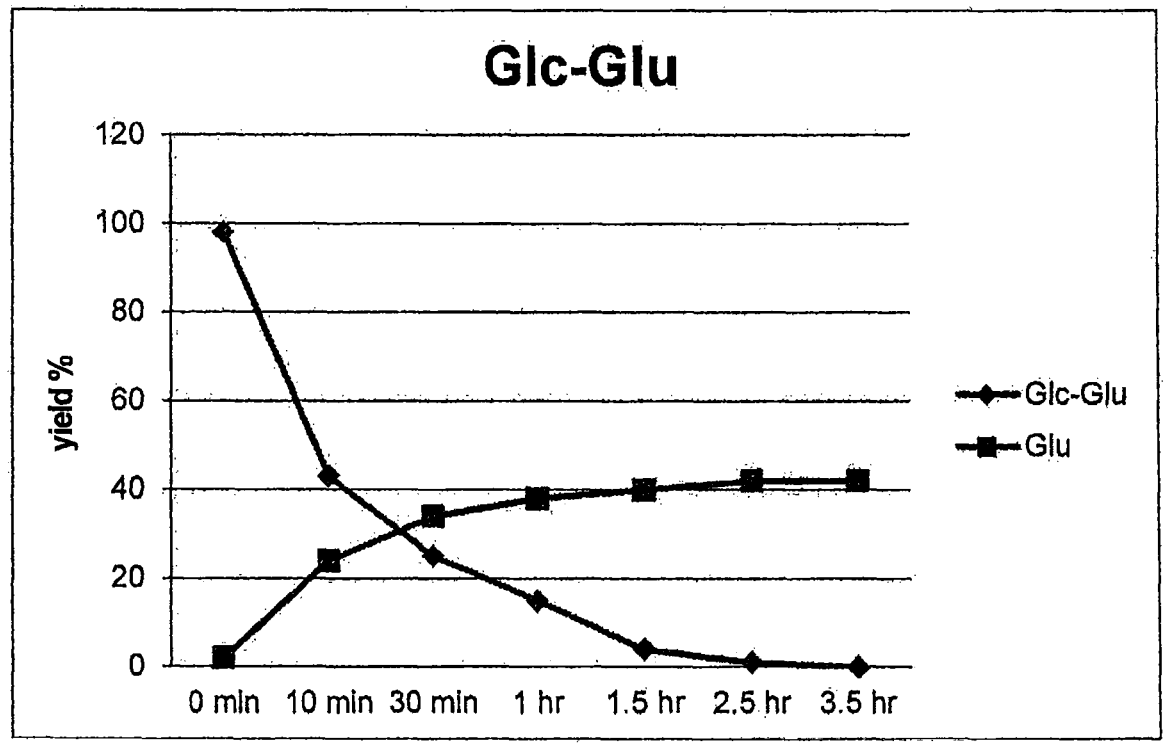
FIG. 8 shows an amino acid production amount by a glucosidase treatment of Glc-Glu.
Figure 9:
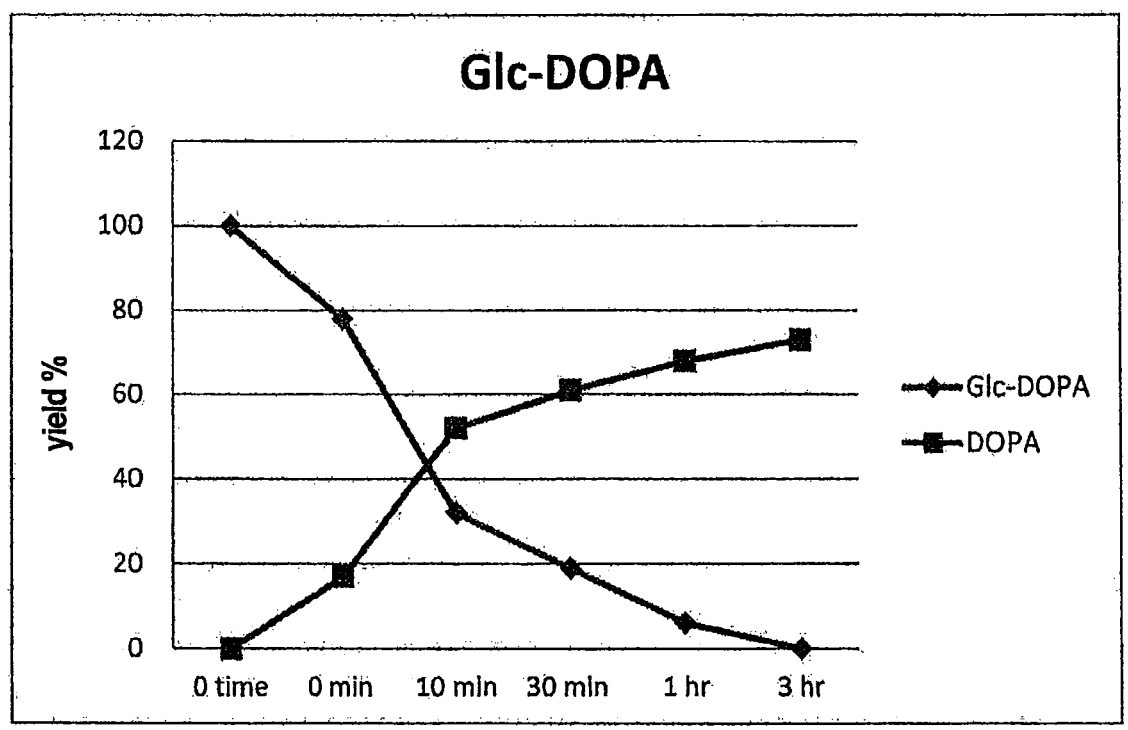
FIG. 9 shows an amino acid production amount by a glucosidase treatment of Glc-DOPA.

Glc-Phe, Glc-Leu, Glc-Lys, Glc-Glu and Glc-DOPA were each dissolved in phosphate buffer (pH 5.5) at the ratio shown in Table 2, α/β-glucosidase in the amount shown in Table 2 was added, and the mixture was stirred in a hot-water bath at 37° C. The mixture was diluted 2-fold with 1% aqueous phosphoric acid solution, and analyzed by HPLC. The results are shown in FIGS. 5-9. As for Glc-Phe, liberation of about 7% of phenylalanine from immediately after addition of the enzyme was confirmed, Glc-Phe almost disappeared 30 min later, and the corresponding phenylalanine was liberated. As for Glc-Leu, about 80% of leucine was liberated 1 hr later; as for Glc-Lys, about 20% of lysine was liberated 1 hr later; as for Glc-Glu, about 40% of glutamic acid was liberated 1 hr later; and as for Glc-DOPA, about 70% of 3,4-dihydroxyphenylalanine was liberated 1 hr later.

TABLE 2

| | glycoamino acid (mg) | phosphate buffer (pH 5.5) (ml) | α-glucosidase (mg) | β-glucosidase (mg) |
|---|---|---|---|---|
| Glc-Phe | 6.3 | 9.5 | 1.9 | 8.3 |
| Glc-Leu | 5.0 | 2.5 | 1.2 | 3.8 |
| Glc-Lys | 1 | 1 | 6.3 | 6.4 |
| Glc-Glu | 5.0 | 5.0 | 6.0 | 2.0 |
| Glc-DOPA | 1.2 | 5.0 | 2.0 | 2.0 |

Experimental Example 3

Leu and Glc-Leu were each added to stirring water (inside temperature 34° C.) in a hot-water bath at 35° C., and the dissolution rate was measured. The amount of the sample added and the measurement results are as shown below (n=2). As compared to Leu, Glc-Leu was dissolved 46 times faster in equal weight and 17 times faster in equimolar amount.

TABLE 3

| | molecular weight | equivalent weight | | equimolar amount to glycoamino acid | |
|---|---|---|---|---|---|
| | | concentration (mg/25 ml water) | dissolution rate | concentration (mg/25 ml water) | dissolution rate |
| Leu | 131.2 | 300 | 20 min 03 sec (1203 sec) | 111 (0.85 mmol) | 7 min 30 sec (450 sec) |
| Glc-Leu | 353.3 | 300 (0.85 mmol) | 26 sec | — | — |

Experimental Example 4

Leu or Glc-Leu was added to water (1 ml) in a thermostatic bath at 25° C. until they remained undissolved, the mixture was stirred for 2 days and the solubility was measured. The concentration was measured by HPLC. As a result, the solubility of Glc-Leu increased 63-fold as compared to that of Leu.

About 1-1.5 g of Glc-DOPA and Glc-Tyr were similarly added to water (0.5 ml) in a thermostatic bath at 25° C. While they were dissolved in water, viscosity thereof was high at this time point and stirring was difficult. Therefore, the samples were diluted, and solubility was measured by HPLC. The solubility of Glc-DOPA was not less than 640-fold as compared to that of DOPA, and the solubility of Glc-Tyr was not less than 4670-fold as compared to that of Tyr.

TABLE 4

| | glycoamino acid (g/100 g water) | amino acid * (g/100 g water) |
|---|---|---|
| Glc-Leu | 334 | 124 |
| Leu | — | 1.96 |
| Glc-DOPA | >498 | >243 |
| DOPA | — | 0.38 |
| Glc-Tyr | >606 | >283 |
| Tyr | — | 0.0607 |

* The weight of amino acid corresponding to the number of moles of dissolved glycoamino acid was calculated.

HPLC analysis conditions were as described below.
column: CAPCELLPAK MG (4.6×250 mm, 5 μm)
column temperature: 40° C.
mobile phase: A: 100 mM $KH_2PO_4$, 5 mM sodium 1-octanesulfonate (pH 2.2)
B: acetonitrile
eluent: Glc-Leu: A/B=90/10, Glc-DOPA, Glc-Tyr: A/B=95/5
flow rate: Glc-DOPA: 1.0 ml/min, Glc-Leu, Glc-Tyr: 1.5 ml/min
detection: photodiode array detector, measurement wavelength 210 nm
injection volume: 10 μL

Experimental Example 5

Since leucine has a unique bitter taste, Glc-Leu was examined by sensory evaluation for its bitter taste masking effect. Three test subjects A, B, C took 0.1 ml of a solution of food additive leucine dissolved in water at a concentration of 0.5% (5000 ppm) with a micropipette, dropped the solution on the tongue, and spit it out to confirm the level of the bitter taste of leucine. Sequentially, the three test subjects A, B, C took 0.1 ml of a solution of Glc-Leu dissolved in water at a concentration of 0.5% (5000 ppm) with a micropipette, dropped the solution on the tongue, and spit it out to compare the level of the bitter taste with that of leucine confirmed earlier. The results are as follows and none of the test subjects felt the bitter taste confirmed with leucine.

TABLE 5

| test subject A | test subject B | test subject C |
|---|---|---|
| no bitter taste | no bitter taste faintly sweet | no bitter taste |

INDUSTRIAL APPLICABILITY

In the glycoamino acid or a salt thereof of the present invention, since a group represented by the formula G-O—C(O)— wherein G is as defined above is introduced into an amino group of the amino acid, the properties (particularly water-solubility, stability in water, bitter taste etc.) that the amino acid itself has are improved, and they are particularly suitable as an aqueous composition or for oral use. In addition, since the above-mentioned group represented by the formula G-O—C(O)— is detached from the amino acid in vivo, the glycoamino acid or a salt thereof of the present invention is highly useful as an amino acid precursor.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

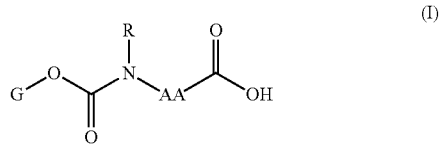

wherein
the moiety —NR-AA-C(=O)OH is an amino acid residue:
G is a sugar residue wherein none of the hydroxyl groups, other than a hydroxyl group bonded to the rest of the molecule, are protected or modified; and
R is a hydrogen atom or an alkyl group,
or a salt of said compound represented by formula (I), wherein the amino acid residue is a residue of an α-amino acid selected from the group consisting of alanine, valine, isoleucine, serine, threonine, cysteine, methionine, glutamic acid, aspartic acid, arginine, histidine, glutamine, asparagine, phenylalanine, tyrosine, tryptophan, cystine, ornithine, thyroxin, praline, and 3,4-dihydroxyphenylalanine,
with the proviso that said compound represented by formula (I) is not:
(1) a compound wherein G is a group represented by formula (II):

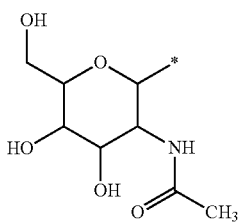

and the moiety —NR-AA-C(=O)OH is a lysine residue or a glutamic acid residue, or
(2) a compound wherein G a group represented by formula (III):

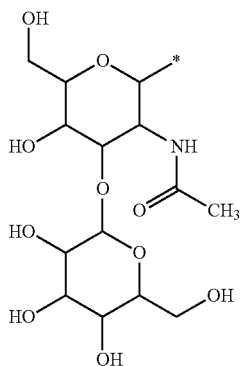

and the moiety —NR-AA-C(O)OH is a serine residue.

2. The compound or salt according to claim 1, wherein the sugar of said sugar residue for G is monosaccharide.

3. The compound or salt according to claim 1, wherein the sugar of said sugar residue for G is glucose, glucosamine, or N-acetylglucosamine.

4. The compound or salt according to claim 1, wherein the moiety represented by formula G-O— has a β-anomer structure.

5. The compound or salt according to claim 1, wherein the amino acid of said amino acid residue is valine, or isoleucine.

6. The compound or salt according to claim 1, wherein the amino acid of said amino acid residue is phenylalanine, tyrosine, or 3,4-dihydroxyphenylalanine.

7. The compound or salt according to claim 1, wherein R is a hydrogen atom.

8. An aqueous composition, comprising a compound represented by formula (I) or salt thereof according to claim 1.

9. An oral preparation, comprising a compound represented by formula (I) or salt thereof according to claim 1.

10. A method of reducing a bitter taste of an amino acid, comprising introducing a group represented by formula G—O—C(O)—, wherein G is a sugar residue wherein none of the hydroxyl groups, other than a hydroxyl group bonded to the rest of the molecule, are protected or modified, into an amino group of amino acid,
wherein
said sugar is a glucose and residue of glucose, and
said amino acid is α-leucine.

11. The method according to claim 10, wherein the moiety represented by formula G-O— has a β-anomer structure.

12. The method according to claim 10, wherein said amino acid in winch a group represented by formula G—O—C(O)— has been introduced is converted to an amino acid in vivo.

13. A method for administering an amino acid to a subject in need thereof, comprising administering a compound represented by formula (I) or salt thereof according to claim 1 to said subject.

* * * * *

UNITED STATES PATENT AND TRADEMARK OFFICE
CERTIFICATE OF CORRECTION

PATENT NO. : 10,787,476 B2
APPLICATION NO. : 15/078305
DATED : September 29, 2020
INVENTOR(S) : Wataru Kurosawa et al.

It is certified that error appears in the above-identified patent and that said Letters Patent is hereby corrected as shown below:

On the Title Page

In Column 1, item (56), U.S. Patent Documents, Line 4, "Mod" should read -- Mori --.

In Column 1, item (56), Other Publications, Line 21, ",(2017)." should read -- , (2017). --.

In the Specification

In Column 9, Line 36, "be m" should read -- be --.

In Column 11, Line 23, "G1cNAc" should read -- GlcNAc --.

In Column 14, Line 20, "acetate-" should read -- acetate= --.

In Column 16, Line 34 (approx.), ")" should read -- ). --.

In Column 16, Line 47, "$^1$H)," should read -- 1H), --.

In Column 16, Line 50, "Hz)" should read -- Hz). --.

In Column 19, Line 10 (approx.), "β-" should read -- β-D- --.

In Column 23, Line 1, "acetate" should read -- acetate= --.

In the Claims

In Column 26, Lines 57-58, Claim 1, "residue:" should read -- residue; --.

In Column 27, Line 2, Claim 1, "praline," should read -- proline, --.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,787,476 B2

In Column 27, Line 22, Claim 1, "G a" should read -- G is a --.

In Column 27, Line 41 (approx.), Claim 1, "C(O)OH" should read -- C(=O)OH --.

In Column 28, Line 10 (approx.), Claim 5, "valine," should read -- valine --.

In Column 28, Line 29 (approx.), Claim 10, "sugar is a glucose and residue of glucose," should read -- sugar residue is a residue of glucose, --.

In Column 28, Line 34 (approx.), Claim 12, "winch" should read -- which --.